(12) United States Patent
Addison et al.

(10) Patent No.: US 11,202,580 B2
(45) Date of Patent: Dec. 21, 2021

(54) COMPENSATION FOR BLOOD PRESSURE SENSOR MOVEMENT

(71) Applicant: Covidien LP, Mansfield, MA (US)

(72) Inventors: Paul S. Addison, Edinburgh (GB); Dean Montgomery, Edinburgh (GB); Andre Antunes, Edinburgh (GB)

(73) Assignee: COVIDIEN LP, Mansfield, MA (US)

( * ) Notice: Subject to any disclaimer, the term of this patent is extended or adjusted under 35 U.S.C. 154(b) by 469 days.

(21) Appl. No.: 16/204,061

(22) Filed: Nov. 29, 2018

(65) Prior Publication Data

US 2020/0170517 A1 Jun. 4, 2020

(51) Int. Cl.
| | |
|---|---|
| *A61B 5/02* | (2006.01) |
| *A61B 5/0225* | (2006.01) |
| *A61B 5/021* | (2006.01) |
| *A61B 5/00* | (2006.01) |
| *A61B 5/11* | (2006.01) |
| A61B 5/0245 | (2006.01) |
| A61B 5/022 | (2006.01) |
| A61B 5/1455 | (2006.01) |

(52) U.S. Cl.
CPC ........ *A61B 5/0225* (2013.01); *A61B 5/02125* (2013.01); *A61B 5/11* (2013.01); *A61B 5/721* (2013.01); *A61B 5/7207* (2013.01); *A61B 5/0245* (2013.01); *A61B 5/02208* (2013.01); *A61B 5/1455* (2013.01); *A61B 2562/046* (2013.01)

(58) Field of Classification Search
CPC ... A61B 5/02156; A61B 5/145; A61B 5/1495; A61B 5/721; A61B 5/11; A61B 5/0245; A61B 5/02208; A61B 2562/046; A61B 5/1455; A61B 5/7275; A61B 5/0215; A61B 5/02028; A61B 5/021; A61B 2560/0223; A61B 2560/0247; A61B 5/7203; A61B 5/7207; A61B 2017/00694; A61B 5/02125

See application file for complete search history.

(56) References Cited

U.S. PATENT DOCUMENTS

| | | | |
|---|---|---|---|
| 6,475,153 B1 * | 11/2002 | Khair ..................... | G08B 25/08 600/485 |
| 6,599,251 B2 | 7/2003 | Chen et al. | |
| 9,861,317 B2 | 1/2018 | Ochs | |
| 2009/0326386 A1 | 12/2009 | Sethi et al. | |
| 2011/0105927 A1 * | 5/2011 | Greenhut ............. | A61N 1/3702 600/513 |

(Continued)

*Primary Examiner* — Andrey Shostak
(74) *Attorney, Agent, or Firm* — Shumaker & Sieffert, P.A.

(57) ABSTRACT

In some examples, devices, systems, and techniques are configured to compensate for changes in sensed blood pressure due to issues such as blood pressure sensor movement. For example, processing circuitry of a device may determine a difference value between a first blood pressure value representative of a blood pressure at a first time and a second blood pressure value representative of the blood pressure at a second time. Responsive to determining that the difference value is greater than or equal to a threshold value, the processing circuitry may generate updated blood pressure values by applying an offset value to the second blood pressure value and subsequently received blood pressure values that compensates for the difference value between the first blood pressure value and the second blood pressure value.

14 Claims, 8 Drawing Sheets

(56) References Cited

U.S. PATENT DOCUMENTS

| | | | |
|---|---|---|---|
| 2012/0136605 A1* | 5/2012 | Addison | A61B 5/7221 702/98 |
| 2012/0198386 A1* | 8/2012 | Hautala | H04N 5/23293 715/838 |
| 2016/0345913 A1* | 12/2016 | Montgomery | A61B 5/7275 |
| 2017/0105631 A1* | 4/2017 | Addison | A61B 5/14553 |
| 2018/0014791 A1 | 1/2018 | Montgomery et al. | |
| 2018/0078155 A1* | 3/2018 | Baek | G16H 50/50 |
| 2018/0338731 A1 | 11/2018 | Addison et al. | |

* cited by examiner

COMPENSATION FOR BLOOD PRESSURE SENSOR MOVEMENT

TECHNICAL FIELD

This disclosure relates to physiological parameter monitoring.

BACKGROUND

Blood pressure is a vital sign of a patient that can be used to monitor cardiovascular status of the patient. Blood pressure can be measured externally, such as using the auscultatory method, which includes detecting Korotkoff sounds and a blood pressure cuff, or using ultrasound techniques. Blood pressure can also be measured internally, such as using a disposable probe that is disposed within an artery and coupled to a pressure transducer (which may be internal or external of the patient).

In some cases, blood pressure may be used to monitor an autoregulation status of a patient, e.g., during a medical procedure. Cerebral autoregulation (CA) is a physiological process that attempts to maintain a desired level of cerebral blood flow over a wide range of blood pressure changes to supply appropriate levels of oxygen and nutrients to the brain. Complex myogenic, neurogenic, and metabolic mechanisms may be involved in CA.

During autoregulation, cerebral arterioles dilate or constrict to maintain optimal blood flow. For example, as blood pressure decreases, cerebral arterioles dilate in an attempt to maintain blood flow. As blood pressure increases, cerebral arterioles constrict to similarly maintain the blood flow that, if left unrestricted, could adversely impact the brain. Intact cerebral autoregulation function occurs over a range of blood pressures defined between a lower limit of autoregulation (LLA) and an upper limit of autoregulation (ULA). If the patient's autoregulation process is not functioning properly, then the patient may experience inappropriate cerebral blood flow, which may have an adverse effect on the patient's health. For example, a drop in cerebral blood flow may cause ischemia. As another example, an increase in cerebral blood flow may cause hyperemia, which may result in swelling of the brain or edema. Autoregulation dysfunction may result from a number of causes including, stroke, traumatic brain injury, brain lesions, brain asphyxia, or infections of the central nervous system.

SUMMARY

This disclosure describes devices, systems, and techniques for compensating for changes in sensed blood pressure due to issues such as blood pressure sensor movement. For example, a pressure probe of a blood pressure sensor placed within a blood vessel may measure a different pressure at a location in the center of the blood vessel compared to the pressure measured at a different location in the blood vessel, e.g., near a wall of the blood vessel. Therefore, movement of the pressure probe during blood pressure monitoring may cause a relatively abrupt change in the measured blood pressure that is caused by the change in location of the pressure probe instead of an actual change (e.g., due to physiological reasons) in the blood pressure of the patient. A system may be configured to identify an abrupt change in blood pressure and compensate for the change. For example, the system may apply an offset equal to the magnitude of the abrupt change to future blood pressures in order to remove the pressure change attributable to the movement of the pressure probe. In other examples, if the blood pressure is compared to one or more thresholds for monitoring a physiological status of the patient (e.g., an autoregulation status), then the system may compensate for the abrupt change by at least adjusting the one or more thresholds according to the identified change in blood pressure.

In one example, a device includes a memory configured to store a first blood pressure value representative of a blood pressure of a patient sensed by a blood pressure sensor at a first time, and processing circuitry configured to receive a second blood pressure value representative of the blood pressure of the patient sensed by the blood pressure sensor at a second time, determine a difference value between the first blood pressure value and the second blood pressure value, determine that the difference value is greater than or equal to a threshold value, responsive to determining that the difference value is greater than or equal to the threshold value, generate an offset value that compensates for the difference value, generate, based on the offset value and subsequently received blood pressure values representative of the blood pressure of the patient sensed after the second time, at least one updated parameter value, and output the at least one updated parameter value.

In another example, a method includes storing, by a memory, a first blood pressure value representative of a blood pressure of a patient sensed by a blood pressure sensor at a first time, receiving, by processing circuitry, a second blood pressure value representative of the blood pressure of the patient sensed by the blood pressure sensor at a second time, determining, by the processing circuitry, a difference value between the first blood pressure value and the second blood pressure value, determining, by the processing circuitry, that the difference value is greater than or equal to a threshold value, responsive to determining that the difference value is greater than or equal to the threshold value, generating, by the processing circuitry, an offset value that compensates for the difference value, generating, by the processing circuitry and based on the offset value and subsequently received blood pressure values representative of the blood pressure of the patient sensed after the second time, at least one updated parameter value, and outputting, by the processing circuitry, the at least one updated parameter value.

In another example, a system includes a memory configured to store a first blood pressure value representative of a blood pressure of a patient sensed by a blood pressure sensor at a first time, a display device configured to display autoregulation information, and processing circuitry configured to receive a second blood pressure value representative of the blood pressure of the patient sensed by the blood pressure sensor at a second time, determine a difference value between the first blood pressure value and the second blood pressure value, determine that the difference value is greater than or equal to a threshold value, responsive to determining that the difference value is greater than or equal to the threshold value, control the display device to present an indication that indicates the autoregulation information based on blood pressure values representing the blood pressure sensed prior to the second time is inaccurate.

The details of one or more examples are set forth in the accompanying drawings and the description below. Other features, objects, and advantages will be apparent from the description and drawings, and from the claims.

DETAILED DESCRIPTION

Figure 1:
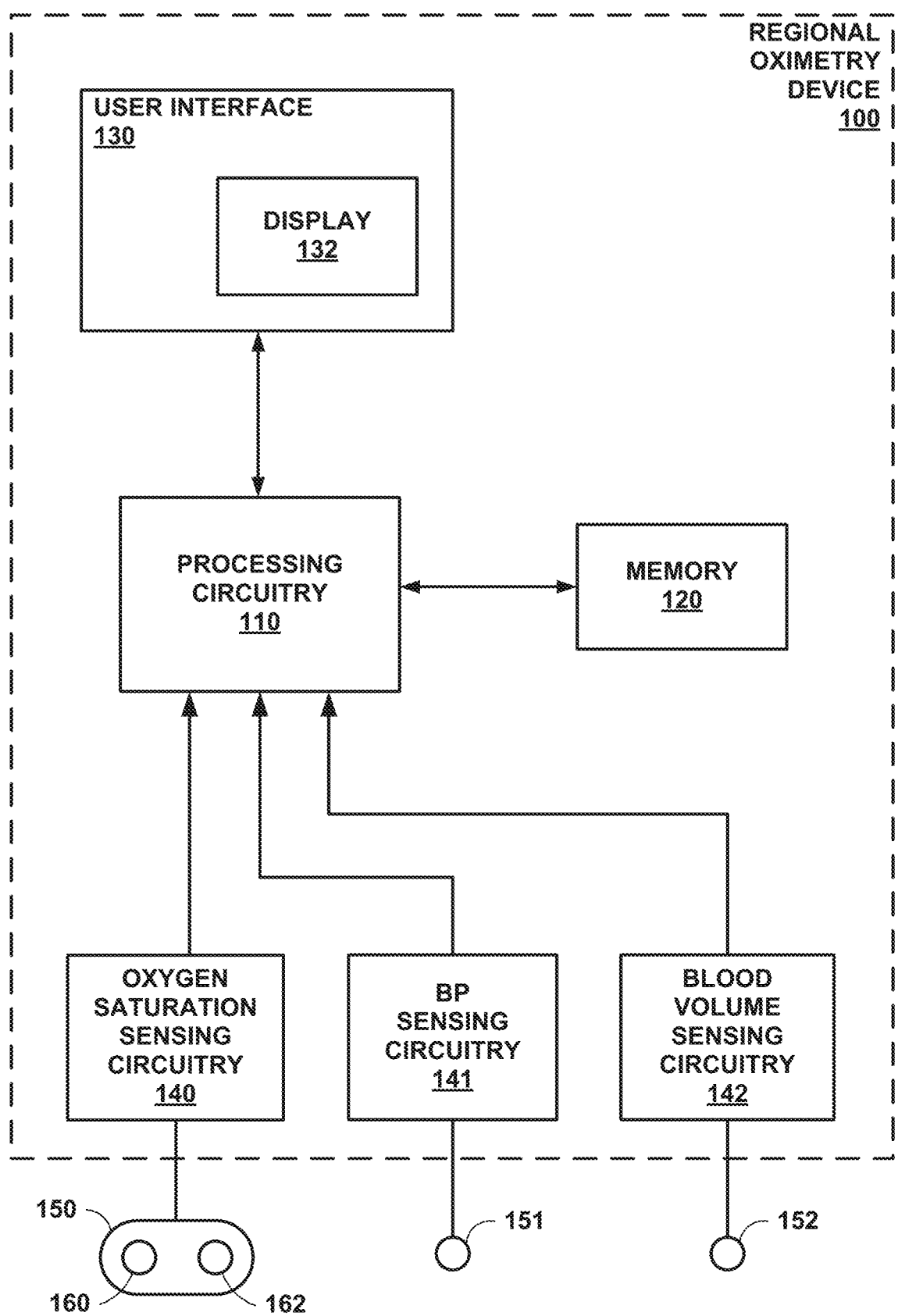
FIG. 1 is a conceptual block diagram illustrating an example regional oximetry device.

This disclosure describes devices, systems, and techniques for compensating for, or mitigating, changes in sensed blood pressure due to issues such as blood pressure sensor movement. Blood pressure can be measured using a sensor (also referred to herein as a blood pressure sensor) that is placed within a blood vessel (e.g., an artery or vein) of a patient. In some examples, a pressure probe of the blood pressure sensor is inserted into the blood vessel and coupled to an electrical circuit of the sensor that remains external from the patient. As the pressure of the blood changes during each cardiac cycle, for example, the sensor can detect these pressure changes as indicative of the blood pressure over time. However, because the actual pressure of the blood at different locations within the vessel may vary depending on the location of the probe with respect to the vessel wall due to complex viscoelastic properties of the vessel and the blood, for example. Therefore, at a given time, the blood pressure sensed by the pressure probe may vary between different locations of the pressure probe within the blood vessel.

The pressure probe may move relative to the patient, e.g., within the blood vessel, due to one or more causes. For example, a subject or object physically touching an external portion of the pressure probe may cause the pressure probe to move within the blood vessel. This movement of the pressure probe may be inadvertent or intentional in order to find a better pressure signal. If the pressure probe moves closer to the blood vessel wall as a result of the external interaction with the probe, then the sensor may indicate that the blood pressure has dropped relatively abruptly. However, this abrupt drop in measured blood pressure (e.g., a step change) was only due to the change in location of the pressure probe instead of due to a physiological change with the patient. For example, a change in blood pressure may be determined to be an abrupt change when the change exceeds (e.g., greater than or less than) a predefined threshold pressure or rate of change in the blood pressure. Other non-physiological causes of abrupt changes in sensed blood pressure may occur as well. This change in blood pressure may incorrectly indicate to a clinician that the patient has experienced a physiological and/or anatomical change that caused the drop in blood pressure. The devices and systems described herein may be configured to identify and/or compensate for this abrupt change in blood pressure in order to prevent the blood pressure change from being inferred as a physiological blood pressure change.

In some examples, devices and systems may calculate one or more physiological parameters based on the measured blood pressure. For example, a system may calculate one or more autoregulation parameters related to an autoregulation status of a patient. The autoregulation status of a patient may be an indication that the cerebral autoregulation control mechanism of the patient is intact (e.g., functioning properly) or impaired (e.g., not functioning properly). A cerebral autoregulation (CA) control mechanism of the body may regulate cerebral blood flow (CBF) over a range of systemic blood pressures. This range of systemic blood pressures indicative of intact CA may lie between a lower limit of autoregulation (LLA) and an upper limit of autoregulation (ULA) (examples of autoregulation parameters). Outside of the LLA and the ULA (e.g., below the LLA and above the ULA), blood pressure directly drives CBF, and CA function may thus be considered impaired.

One method to determine the limits of autoregulation (e.g., the LLA and ULA) noninvasively using near-infrared spectroscopy (NIRS) technology may include the cerebral oximetry index (COx) measure, which is a moving correlation index between an arterial pressure measurement, e.g., a mean arterial pressure (MAP), and regional oxygen saturation ($rSO_2$). For example, the COx measure (e.g., using the Pearson coefficient) is derived from the correlation between $rSO_2$ and MAP. COx relates to the regression line fit or linear correlation between $rSO_2$ and MAP over a time window, such as three hundred seconds in some examples. The COx method may be used to produce a representation of a patient's blood-pressure-dependent autoregulation status. When the CA is intact for a patient, there is typically no correlation between MAP and $rSO_2$. In contrast, MAP and $rSO_2$ typically directly correlate (e.g., the correlation index of COx is approximately 1) when the CA is impaired. In practice, however, sensed data indicative of autoregulation may be noisy and/or there might be a slightly correlated relationship between variables (e.g., MAP and $rSO_2$) even when CA is intact for the patient.

Some existing systems for determining autoregulation parameter values and monitoring autoregulation may determine a patient's autoregulation status based on various physiological parameter values (also referred to herein as physiological values). One of these physiological values is the measured blood pressure of the patient. As discussed above, movement of a blood pressure sensor (which may be movement of the pressure probe of the sensor that is placed within a blood vessel of the patient) can cause an abrupt change in the measured blood pressure. Since the system may monitor the measured blood pressure with respect to the LLA and ULA to determine the autoregulation status and determine the LLA and ULA based on the measured blood pressure, an abrupt change in the measured blood pressure that is not reflective of a physiological change may result in an inaccurate determination of the autoregulation status for the patient.

For example, if the pressure probe moves within the patient and results in a drop in measured blood pressure, the system may inaccurately indicate that the patient's autoregulation status is impaired when the patient is actually is still maintaining an intact autoregulation status. Similarly, an abrupt increase in measured blood pressure may exceed the ULA and incorrectly indicate that the patient's autoregulation status has changed to impaired. These inaccurate autoregulation status indications resulting from the abrupt change in blood pressure may cause a clinician to take corrective action that is not necessary. Put another way, a system that compensates for the change abrupt changes to blood pressure that is not physiological may avoid unnecessary corrective action that a physician may otherwise perform. The devices and systems described herein may be configured to identify and/or compensate for this abrupt change in blood pressure in order to prevent the blood pressure change from being inferred as a physiological blood pressure change. The compensation action for the change in measured blood pressure may involve correcting or offsetting the measured blood pressure and/or correcting or offsetting the ULA and/or LLA calculated by the system.

As described herein, a monitoring system (or device) may be configured to identify an abrupt change in blood pressure that is not indicative of an actual physiological change in the patient and compensate for, or mitigate, the change. For example, the system may detect the abrupt change when the measured blood pressure changes a threshold amount or more than the threshold amount over a predetermined period of time. This threshold amount may be a rate of blood pressure change and/or a threshold magnitude change between two or more blood pressure samples within the period of time. In some examples, the system may apply an offset equal to the magnitude of the abrupt change to future blood pressure measurements in order to remove the pressure change due to the movement of the pressure probe. For example, if the abrupt change in measured blood pressure is calculated to be an increase of 8 mmHg, then the system may reduce future measured blood pressures by 8 mmHg. For a system that monitors the blood pressure with respect to the LLA and ULA, the system can continue to use the previously determined LLA and ULA and, in some cases, also calculate future LLA and ULA values with the adjusted measured blood pressures. Since historical blood pressures may be used to calculate the LLA and ULA, a system that compensates for an abrupt change in measured blood pressure and retains the ability to continue to use the same historical blood pressures may make the system operate more efficiently (e.g., not need to re-obtain blood pressure measurements) and continue to provide accurate information regarding the patient (e.g., avoid a lapse in ULA or LLA calculations due to collection of more blood pressure measurements).

Alternatively, if the measured blood pressure is compared to one or more thresholds for monitoring a physiological status of the patient (e.g., the LLA and ULA for autoregulation monitoring), the system may continue to use the measured blood pressures without an offset. However, the system may compensate for the abrupt change by adjusting the LLA and/or ULA according to the identified change in blood pressure. For example, if the abrupt change in measured blood pressure is calculated to be an increase of 8 mmHg, then the system may increase both the LLA and ULA by 8 mmHg. Therefore, even though the blood pressure has artificially changed, the system may be configured to continue to correctly monitor the autoregulation status of the patient. In some examples, the system may employ a combination of adjustments to future blood pressure values and adjustments to the LLA and ULA for continued monitoring.

In some cases, movement of the pressure probe relative to the blood vessel or other blood pressure measurement-related issues may not present as a singular abrupt change in magnitude in a single direction of the measured blood pressure. Instead, the abrupt change may include one or more bounces in measured blood pressure (e.g., ringing) as the pressure probe settles at its new location. Therefore, in some examples, the system may, in response to detecting a supra-threshold change in the blood pressure, monitor for any bounces in blood pressure values after the abrupt change. The system may then determine the magnitude of the abrupt change as the total change in blood pressure from prior to the abrupt change to the blood pressure at which no further bounces are identified.

Processing circuitry of the devices, systems, and techniques of this disclosure may provide an improved graphical user interface with more accurate information relating to the blood pressure and/or CA of the patient. The processing circuitry may present a clinician with an indication of the CA status of the patient that is unaffected, or non-substantially affected, by abrupt changes to blood pressure caused by non-physiological issues such as a moved pressure probe. In addition, this disclosure describes techniques implemented by devices or systems that enable the devices or systems to compensate for or mitigate errors in blood pressure sensor data, which, as noted above, may be erroneous in that a change in sensed blood pressure values may not entirely be due to physiological changes but rather due (at least in part) to blood pressure sensor movement relative to the patient. In this manner, these devices or systems may be configured to continue to present more accurate clinical information regarding a patient despite measurement errors that can occur.

FIG. 1 is a conceptual block diagram illustrating an example regional oximetry device 100. Regional oximetry device 100 includes processing circuitry 110, memory 120, user interface 130, display 132, sensing circuitry 140, 141, and 142, and sensing device(s) 150, 151, and 152. In some examples, regional oximetry device 100 may be configured to determine and display the cerebral autoregulation status of a patient, e.g., during a medical procedure or for more long-term monitoring, such as monitoring of prenatal infants, children, or adults. A clinician may receive information regarding the cerebral autoregulation status of a patient via display 132 and adjust treatment or therapy to the patient based on the cerebral autoregulation status information. Although regional oximetry device 100 is described as an example device herein, other devices may calculate blood pressure and/or use blood pressure for other physiological monitoring and perform similar a compensation process on blood pressures subjected to abrupt changes in the measured blood pressure values.

Processing circuitry 110 as well as other processors, processing circuitry, controllers, control circuitry, and the like, described herein, may include one or more processors. Processing circuitry 110 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 110 may include multiple components, such as any combination of one or more microprocessors, one or more DSPs, one or more ASICs, or one or more FPGAs, as well as other discrete or integrated logic circuitry, and/or analog circuitry.

Memory 120 may be configured to store measurements of blood pressure, oxygen saturation, blood volume, other physiological parameters, relationships between blood pressure and physiological parameters, MAP values, $rSO_2$ values, COx values, BVS values, HVx values, and/or value(s) of an LLA and/or a ULA, for example. Memory 120 may also be configured to store data such as thresholds for detecting abrupt changes in blood pressure, previous LLA and ULA values, and/or other physiological parameters and expected values of physiological parameters. Memory 120 may also be configured to store data such as threshold levels for physiological parameters, threshold values for blood pressure, and/or threshold levels for signal quality metrics. The thresholds or other data may stay constant throughout the use of device 100 and across multiple patients, or these values may change over time.

In some examples, memory 120 may store program instructions, which may include one or more program modules, which are executable by processing circuitry 110. When executed by processing circuitry 110, such program instructions may cause processing circuitry 110 to provide the functionality ascribed to it herein. For example, memory 120 may store instructions regarding how to determine abrupt changes in measured blood pressure, calculating ULA and LLA values, and presenting information to the user via user interface 130. The program instructions may be embodied in software, firmware, and/or RAMware. Memory 120, as well as other memory devices described herein (e.g., memory 220 shown in FIG. 2), may include any volatile, non-volatile, magnetic, optical, circuitry, or electrical media, such as a random access memory (RAM), read-only memory (ROM), non-volatile RAM (NVRAM), electrically-erasable programmable ROM (EEPROM), flash memory, or any other digital media.

User interface 130 and/or display 132 may be configured to present information to a user (e.g., a clinician). User interface 130 and/or display 132 may be configured to present a graphical user interface to a user, where each graphical user interface may include indications of values of one or more physiological parameters of a subject. For example, processing circuitry 110 may be configured to present blood pressure values, other physiological parameter values (e.g., heart rate), and indications of cerebral autoregulation status of a patient via display 132. In some examples, if processing circuitry 110 determines that the cerebral autoregulation status of the patient is impaired, then processing circuitry 110 may present a notification (e.g., an alert) indicating the impaired cerebral autoregulation status via display 132. As another example, processing circuitry 110 may present, via display 132, estimates of regional oxygen saturation ($rSO_2$) for a patient, an estimate of the blood oxygen saturation ($SpO_2$) determined by processing circuitry 110, pulse rate information, respiration rate information, blood pressure, any other patient parameters, or any combination thereof.

User interface 130 and/or display 132 may include a monitor, cathode ray tube display, a flat panel display such as a liquid crystal (LCD) display, a plasma display, or a light emitting diode (LED) display, personal digital assistant, mobile phone, tablet computer, laptop computer, any other suitable display device, or any combination thereof. User interface 130 may also include means for projecting audio to a user, such as speaker(s). Processing circuitry 110 may be configured to present, via user interface 130, a visual, audible, or somatosensory notification (e.g., an alarm signal) indicative of the patient's autoregulation status. User interface 130 may include or be part of any suitable device for conveying such information, including a computer workstation, a server, a desktop, a notebook, a laptop, a handheld computer, a mobile device, or the like. In some examples, processing circuitry 110 and user interface 130 may be part of the same device or supported within one housing (e.g., a computer or monitor).

Sensing circuitry 140, 141, and 142 may be configured to receive physiological signals sensed by respective sensing device(s) 150, 151, and 152 and communicate the physiological signals to processing circuitry 110. Sensing device(s) 150, 151, and 152 may include any sensing hardware configured to sense a physiological parameter of a patient, such as, but not limited to, one or more electrodes, optical receivers, blood pressure cuffs, or the like. Sensing circuitry 140, 141, and 142 may convert the physiological signals to usable signals for processing circuitry 110, such that processing circuitry 110 is configured to receive signals generated by sensing circuitry 140, 141, and 142. Sensing circuitry 140, 141, and 142 may receive signals indicating physiological parameters from a patient, such as, but not limited to, blood pressure, regional oxygen saturation, heart rate, and respiration. Sensing circuitry 140, 141, and 142 may include, but are not limited to, blood pressure sensing circuitry, oxygen saturation sensing circuitry, heart rate sensing circuitry, temperature sensing circuitry, electrocardiography (ECG) sensing circuitry, electroencephalogram (EEG) sensing circuitry, or any combination thereof. In some examples, sensing circuitry 140, 141, and 142 and/or processing circuitry 110 may include signal processing circuitry such as an analog-to-digital converter.

In some examples, oxygen saturation sensing device 150 is a regional oxygen saturation sensor configured to generate an oxygen saturation signal indicative of blood oxygen saturation within the venous, arterial, and/or capillary systems within a region of the patient. For example, oxygen saturation sensing device 150 may be configured to be placed on the patient's forehead and may be used to determine the oxygen saturation of the patient's blood within the venous, arterial, and/or capillary systems of a region underlying the patient's forehead (e.g., in the cerebral cortex).

In such cases, oxygen saturation sensing device 150 may include emitter 160 and detector 162. Emitter 160 may include at least two light emitting diodes (LEDs), each configured to emit at different wavelengths of light, e.g., red or near infrared light. In some examples, light drive circuitry (e.g., within sensing device 150, sensing circuitry 140, and/or processing circuitry 110) may provide a light drive signal to drive emitter 160 and to cause emitter 160 to emit light. In some examples, the LEDs of emitter 160 emit light in the wavelength range of about 600 nanometers (nm) to about 1000 nm. In a particular example, one LED of emitter 160 is configured to emit light at a wavelength of about 730 nm and the other LED of emitter 160 is configured to emit light at a wavelength of about 810 nm. Other wavelengths of light may also be used in other examples.

Detector 162 may include a first detection element positioned relatively "close" (e.g., proximal) to emitter 160 and a second detection element positioned relatively "far" (e.g., distal) from emitter 160 (these multiple detectors are shown as a single detector in the example of FIG. 1). Light intensity of multiple wavelengths may be received at both the "close" and the "far" detector 162. For example, if two wavelengths are used, the two wavelengths may be contrasted at each location and the resulting signals may be contrasted to arrive at a regional saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). Surface data from the skin and skull may be subtracted out, to generate a regional oxygen saturation signal for the target tissues over time. Oxygen saturation sensing device 150 may provide the regional oxygen saturation signal to processing circuitry 110 or to any other suitable processing device to enable evaluation of the patient's autoregulation status.

In operation, blood pressure sensing device 151 and oxygen saturation sensing device 150 may each be placed on the same or different parts of the patient's body. For example, blood pressure sensing device 151 and oxygen saturation sensing device 150 may physically separate from each other and separately placed on the patient. As another example, blood pressure sensing device 151 and oxygen saturation sensing device 150 may in some cases be part of the same sensor or supported by a single sensor housing. For example, blood pressure sensing device 151 and oxygen saturation sensing device 150 may be part of an integrated oximetry system configured to non-invasively measure blood pressure (e.g., based on time delays in a PPG signal) and regional oxygen saturation. One or both of blood pressure sensing device 151 or oxygen saturation sensing device 150 may be further configured to measure other parameters, such as hemoglobin, respiratory rate, respiratory effort, heart rate, saturation pattern detection, response to stimulus such as bispectral index (BIS) or electromyography (EMG) response to electrical stimulus, or the like. While an example regional oximetry device 100 is shown in FIG. 1, the components illustrated in FIG. 1 are not intended to be limiting. Additional or alternative components and/or implementations may be used in other examples.

Blood pressure sensing device 151 may be any sensor or device configured to obtain the patient's blood pressure (e.g., arterial blood pressure). In one example, the blood pressure sensing device 151 may include or be connected to a probe configured to be inserted into a blood pressure of the patient. In another example, blood pressure sensing device 151 may include a blood pressure cuff for non-invasively monitoring blood pressure or an arterial line for invasively monitoring blood pressure (e.g., a pressure probe configured to be placed within an artery or vein). In certain examples, blood pressure sensing device 151 may include one or more pulse oximetry sensors. In some such cases, the patient's blood pressure may be derived by processing time delays between two or more characteristic points within a single plethysmography (PPG) signal obtained from a single pulse oximetry sensor.

Additional example details of deriving blood pressure based on a comparison of time delays between certain components of a single PPG signal obtained from a single pulse oximetry sensor are described in commonly assigned U.S. Patent Application Publication No. 2009/0326386 filed Sep. 30, 2008, and entitled "Systems and Methods for Non-Invasive Blood Pressure Monitoring," the entire content of which is incorporated herein by reference. In other cases, the patient's blood pressure may be continuously, non-invasively monitored via multiple pulse oximetry sensors placed at multiple locations on the patient's body. As described in commonly assigned U.S. Pat. No. 6,599,251, entitled "Continuous Non-invasive Blood Pressure Monitoring Method and Apparatus," the entire content of which is incorporated herein by reference, multiple PPG signals may be obtained from the multiple pulse oximetry sensors, and the PPG signals may be compared against one another to estimate the patient's blood pressure. Regardless of its form, blood pressure sensing device 151 may be configured to generate a blood pressure signal indicative of the patient's blood pressure (e.g., arterial blood pressure) over time. Blood pressure sensing device 151 may provide the blood pressure signal to sensing circuitry 141, processing circuitry 110, or to any other suitable processing device to enable evaluation of the patient's cerebral autoregulation status.

Processing circuitry 110 may be configured to receive one or more physiological signals generated by sensing devices 150, 151, and 152 and sensing circuitry 140, 141, and 142. The physiological signals may include a signal indicating blood pressure, a signal indicating oxygen saturation, and/or a signal indicating blood volume of a patient. Processing circuitry 110 may be configured to determine a relationship between blood pressure values of the patient and a physiological parameter of the patient, such as a correlation index (e.g., COx, a hemoglobin volume index (HVx)), an oxygen saturation value, a blood volume value, a gradient-based metric of two or more physiological parameters, and/or another physiological parameter. Processing circuitry 110 can determine a gradients-based metric by determining respective gradients of signals for physiological parameters and determining whether the respective gradients trend together. These gradients may be used in a technique to indicate the CA status as described in, for example, U.S. Patent Application No. 2018/0014791 by Montgomery et al., entitled "SYSTEMS AND METHODS OF MONITORING AUTOREGULATION," and filed on Jul. 13, 2017, which is incorporated herein by reference in its entirety.

Processing circuitry 110 may be configured to determine the blood pressure values for which the physiological parameter is less than or greater than one or more threshold values. As an example, processing circuitry 110 may determine an estimate of the lower limit of cerebral autoregulation (LLA) based on the lowest blood pressure value at which the expected value of COx is less than a threshold value, such as 0.5, 0.4, 0.3, 0.2, 0.1, or 0.0 (e.g., wherein 1.0 represents full correlation and 0.0 represents no correlation between blood pressure and $rSO_2$). Thus, processing circuitry 110 may determine estimates of the limits of cerebral autoregulation (e.g., the LLA and the ULA) based on the blood pressure and $rSO_2$. Additional example details of determining LLA and/or ULA and cerebral autoregulation status may be found in commonly assigned U.S. Patent Application Publication No. 2018/0014791 filed on Jul. 13, 2017, and entitled "Systems and Methods of Monitoring Autoregulation," and commonly assigned U.S. Provisional Patent Application No. 62/510,303 filed on May 24, 2017, and entitled "Determining a Limit of Autoregulation," the entire contents of each of which are incorporated herein by reference.

Processing circuitry 110 may be configured to determine that the patient has an intact CA based on determining that a most recent blood pressure value of the patient is between the upper and lower limits of cerebral autoregulation. In addition, the LLA and ULA may be continually calculated and updated based on newly measured blood pressure values and COx values. Since abrupt changes in the measured blood pressure from issues with measurement hardware (e.g., pressure probe location or pressure cuff deformation) will be used by processing circuitry 110 to determine the blood pressure, LLA, ULA, and overall autoregulation status, the processes described herein for compensating or mitigating errors in blood pressure measurement may enable more accurate monitoring of the patient despite these issues with blood pressure measurement.

For example, a device such as regional oximetry device 100 may include memory circuitry (e.g., memory 120) configured to store a first blood pressure value representative of a blood pressure of a patient sensed by a blood pressure sensor at a first time. Device 100 may also include processing circuitry (e.g., processing circuitry 110) that is configured to receive a second blood pressure value representative of the blood pressure of the patient sensed by the blood pressure sensor at a second time (after the first time) and determine a difference value between the first blood pressure value and the second blood pressure value. The difference value may be an absolute magnitude of blood pressure (e.g., 10 mmHg) or a rate of change of blood pressure (e.g., 30 mmHg per second). Processing circuitry 110 may then determine that the difference value is greater than or equal to a threshold value. The threshold value may be a blood pressure value (e.g., 10 mmHg), a rate of change in blood pressure, blood pressure value change between a certain number of blood pressure measurement samples, or any other type of threshold. In the case of a rate of change, the difference value may be a difference rate of change of the difference value over a period of time between the first time and the second time, wherein the threshold comprises a threshold rate of change. In other examples, the threshold value may be a formula or other complex threshold that incorporates values such as the measured blood pressure change and/or a rate of change in the blood pressure (e.g., a blood pressure change may be determined to be abrupt when both the magnitude of the difference and the rate of change exceeds respective thresholds).

In some examples, in response to determining that the difference value is greater than or equal to the threshold value, processing circuitry 110 may generate an offset value that compensates for the difference value between the first blood pressure value and the second blood pressure. The offset value may be an additive inverse of the difference value (or of the magnitude of the change in blood pressure corresponding to a supra-threshold rate of change in blood pressure). For example, the offset value may be −10 mmHg if the measured blood pressure had an identified increase in blood pressure of 10 mmHg. In other examples, the offset value may differ from the additive inverse of the difference value.

Processing circuitry 110 may then generate at least one updated parameter value. The at least one updated parameter value may be determined based on the offset value and subsequently received blood pressure values representative of the blood pressure of the patient sensed after the second time. Since the blood pressures sensed after the second time will have been affected by the abrupt change in measured blood pressure, the offset value may be used to "correct" or otherwise compensate for the difference value reflected in these affected measured blood pressures. For example, the updated parameter value may be an updated blood pressure value for which the offset value is directly added to the measured blood pressure values. As another example, processing circuitry 110 may determine another updated parameter value, such as an updated LLA value or updated ULA value by adding the offset value to the previously calculated LLA or ULA values to essentially adjust the LLA or ULA threshold to the affected blood pressure values. In this manner, processing circuitry 110 may still identify intact or impaired autoregulation for the patient using previously determined LLA and ULA values even though the measured blood pressure values may have changed. Processing circuitry 110 may then output the at least one updated parameter value. For example, processing circuitry 110 may transmit the at least one updated parameter values to another device for monitoring or other calculations, or processing circuitry 110 may control a display device to display a representation of the updated parameter values.

As discussed above, in one example, the updated parameter value may be an updated blood pressure value. Processing circuitry 110 may be configured to generate the updated blood pressure values by at least applying the offset value to the second blood pressure value and the subsequently received blood pressure values representative of the blood pressure of the patient sensed after the second time. In other words, the offset value may be applied to the affected blood pressure values measured after the detected abrupt change in blood pressure values.

Alternatively, or additionally, the updated parameter value may be at least one of an updated LLA value or an updated ULA value. Processing circuitry 110 may be configured to generate at least one of the updated LLA value or the updated ULA value by at least applying the offset value to at least one of a determined LLA value or a determined ULA value based on the subsequently received blood pressure values representative of the blood pressure of the patient sensed after the second time. For example, if the measured blood pressure values have increased due to movement of the pressure probe, then the LLA and ULA previously used to monitor autoregulation of a patient may no longer be accurate. However, applying the offset value to the LLA and ULA values calculated based on the new, higher, blood pressure values may maintain help the validity of the LLA and ULA thresholds for determining the autoregulation status of the patient. In one example, processing circuitry 110 may be configured to control a display device to display at least one of the updated LLA value or the updated ULA value moving forward after the abrupt change in blood pressure and display at least one of a prior LLA value or a prior ULA value generated based on blood pressure values representative of blood pressure sensed prior to the second time. In this manner, the LLA and ULA values displayed on the screen will be different before and after the point in time that the abrupt change in measured blood pressure occurred.

In some examples in which processing circuitry 110 does not apply the offset value to blood pressure values measured after the detected abrupt change, processing circuitry 110 may determine the updated LLA values and updated ULA values based on the unchanged measured blood pressure values and downweighted blood pressure values representative of the blood pressure sensed prior to the second time. In other words, processing circuitry 110 may determine LLA and ULA values multiple blood pressure values sensed over time. After processing circuitry 110 identifies an abrupt change in measured blood pressure (e.g., a change in measured blood pressure that is identified as associated with probe movement instead of physiological changes), the previously measured blood pressure values are less relevant to updated LLA values and updated ULA values calculated using the offset value. Therefore, processing circuitry 110 may reduce the weighting of the prior blood pressure values to reduce the impact of these pre-abrupt change blood pressure values from affecting the updated LLA values and updated ULA values.

In some examples, the pressure probe of blood pressure sensor 151 that can be placed within the blood vessel may include an accelerometer or other movement sensor configured to generate a signal (referred to herein as a movement signal) indicative of movement of the pressure probe within the blood vessel. In these examples, processing circuitry 110 may be configured to receive a movement signal from blood pressure sensor 151 representative of movement of a probe of blood pressure sensor 151, which may indicate movement of the probe with respect to the blood vessel within which the probe is disposed. Processing circuitry 110 may compare a characteristic of the movement signal to a movement threshold and determine that the movement signal is greater than or equal to the movement threshold. The characteristic can include, for example, a discrete amplitude, a peak, mean, or lowest amplitude for a predetermined range of time, a frequency of the signal, a frequency band (e.g., fundamental frequency) component of the signal, or the like.

In response to determining that the characteristic of the movement signal is greater than or equal to the movement threshold and the difference value calculated for the change in the blood pressure is greater than or equal to the threshold value, processing circuitry 110 may generate the offset value that compensates for the difference value determined between the first blood pressure value and the second blood pressure. In this manner, the movement signal may help processing circuitry 110 distinguish between abrupt changes in blood pressure that may be physiological and those abrupt changes in blood pressure caused by movement of the pressure prove or other non-physiological cause of the change in blood pressure.

In some examples, device 100 may present via user interface 130 an indication that the pressure probe has moved or the displayed information related to blood pressure may be compromised due to an issue such as pressure probe movement. These indications may be in addition to, or instead of, adjusting a parameter value such as the blood pressure, LLA, or ULA based on an offset value. In other words, the presented indications that the pressure probe may have moved may indicate that the blood pressure measurements, or information based on the blood pressure measurements, may be inaccurate. For example, processing circuitry 110 may be configured to, in response to determining that the difference value is greater than or equal to the threshold value, control display 132 of user interface 130 to present a notification (e.g., a warning) that indicates autoregulation information determined based on blood pressure values received prior to the second time is inaccurate. This warning could be in the form of a visual indication (e.g., change of color of a visual indicia, text, arrows, etc.), audible alert, or tactile alert.

In other examples, processing circuitry 110 may be configured to, in response to determining that the second blood pressure is greater than or equal to the threshold value, control the user interface to display first autoregulation information (e.g., prior determined LLA and ULA values) generated based on blood pressure values representing the blood pressure sensed prior to the second time in greyscale (or other color) and also display second autoregulation information (e.g., updated LLA and ULA values) generated based on blood pressure values representing the blood pressure sensed after, and including, the second time in one or more colors different than the greyscale (or the other color). In this manner, the change in color of the displayed LLA and ULA values may indicate to the user which autoregulation information is currently relevant to the sensed blood pressure values. In other examples, processing circuitry 110 may be configured to, in response to determining that the second blood pressure exceeds the threshold value, control a user interface to present a warning that indicates a blood pressure anomaly due to movement of a probe of the blood pressure sensor within the patient. In some examples, this notification may reference a point in time at which the abrupt change in blood pressure occurred so that the user can quickly identify why the abrupt change in blood pressure may have occurred at that time.

In some examples, processing circuitry 110 may employ a process for analyzing the blood pressure signal (e.g., two or more blood pressure values that may be discrete or an analog signal) for characteristics indicative of pressure prove movement. For example, processing circuitry 110 may identify probe movement in response to detecting type of waveform shape, number of waves over a certain period of time, waveform frequency, spectral analysis of the waveform, or any other type of criteria. Processing circuitry 110 may employ such a process to differentiate probe movement or other sensor issues from physiological changes that may have manifested as the change to measured blood pressure.

Figure 5:
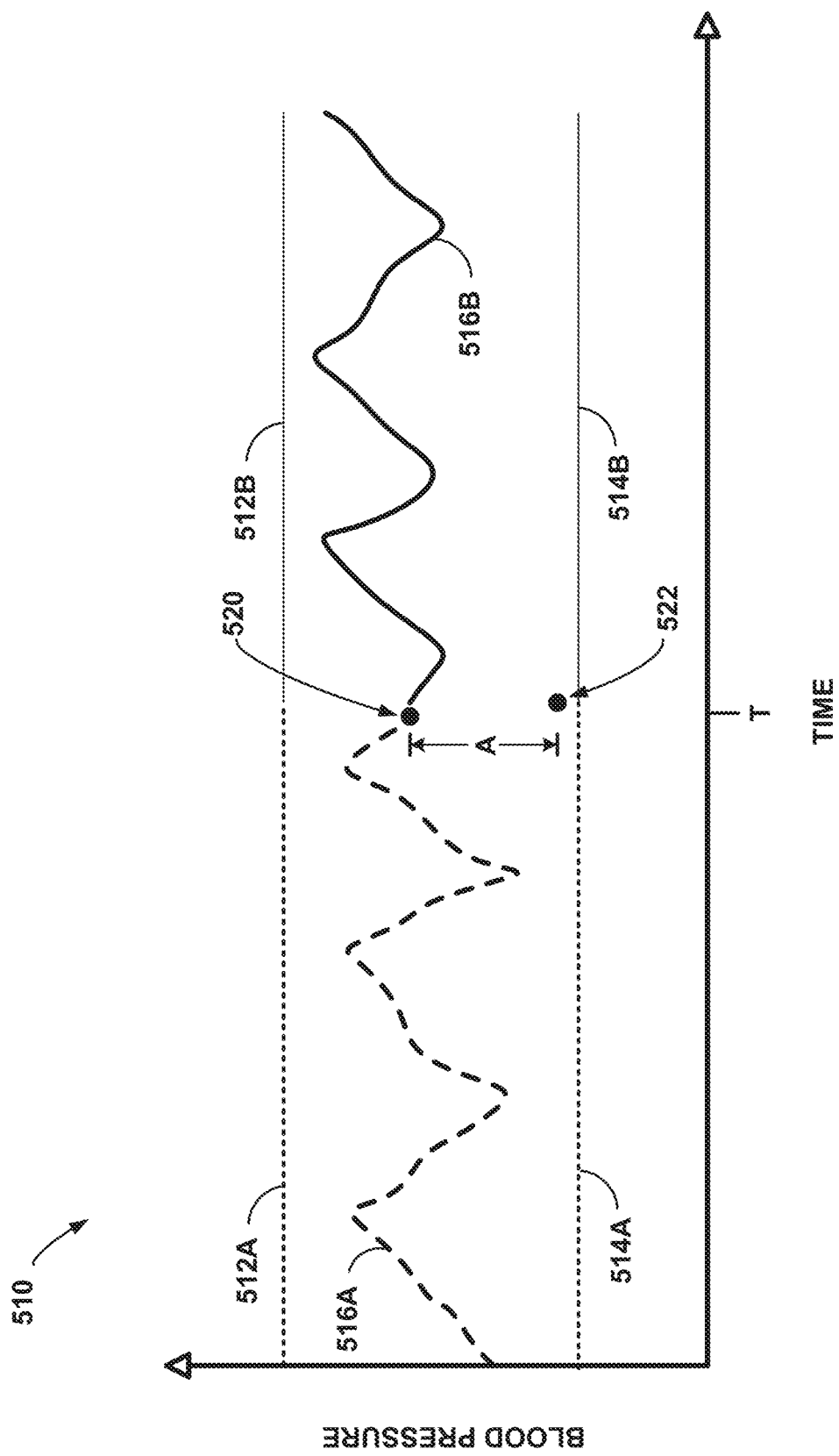
FIG. 5 is a graph illustrating an example blood pressure, lower limit of autoregulation (LLA), and upper level of autoregulation (ULA) when blood pressure is adjusted to compensate for an abrupt change in measured blood pressure.
Figure 7:
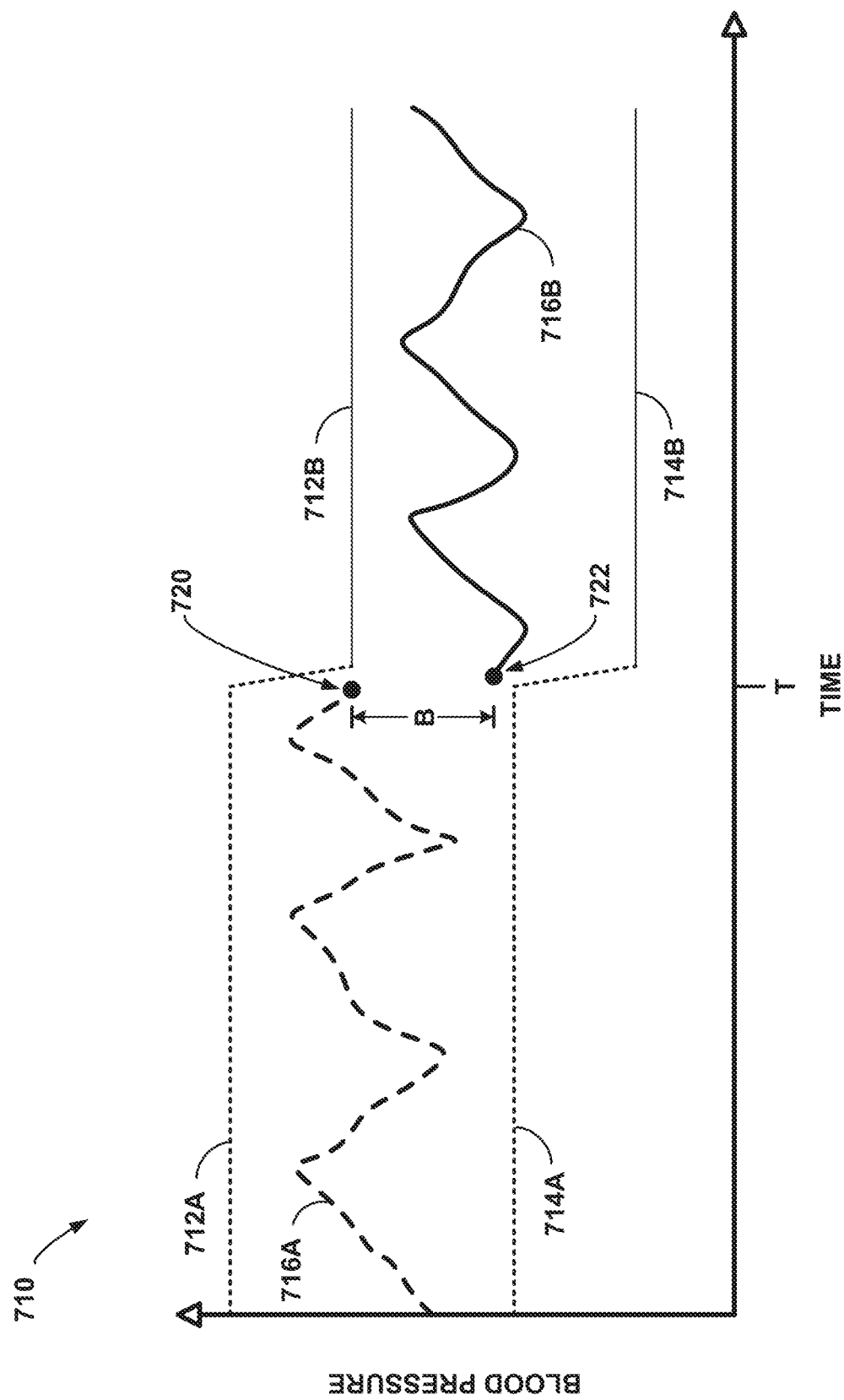
FIG. 7 is a graph illustrating an example blood pressure, LLA, and ULA when the LLA and ULA are adjusted to compensate for an abrupt change in measured blood pressure.

In other examples, user interface 130 may receive user input from the clinician or other user indicating that pressure probe has moved within the patient or that some other sensor issue was identified. Processing circuitry 110 may compensate for any changes to the measured blood pressure in response to receiving this input. In some examples of receiving user input that the prove has been moved, processing circuitry 110 may even compensate for the changes to measured blood pressure that do not exceed the predetermined threshold. In other words, processing circuitry 110 may treat the user input as a command to reset the blood pressure values and/or LLA or ULA values. Similarly, processing circuitry 110 may be configured to receive user input that controls how processing circuitry 110 should compensate for an abrupt change in measured blood pressure. For example, processing circuitry 110 may receive user input that selects between adjusting the blood pressures (as shown in FIG. 5) and adjusting another parameter value (e.g., LLA and ULA as shown in FIG. 7).

The measured blood pressure values described herein may be rate blood pressure values indicative of the exact blood pressure at any given time (e.g., blood pressure values that indicate the blood pressure changes within a cardiac cycle). In other examples, the measured blood pressure values may refer to an average blood pressure, such as a mean arterial pressure (MAP) in which discrete blood pressure measurements have been taken and used to calculate an average pressure that does not identify intra-cardiac cycle blood pressure variations.

Figure 2:
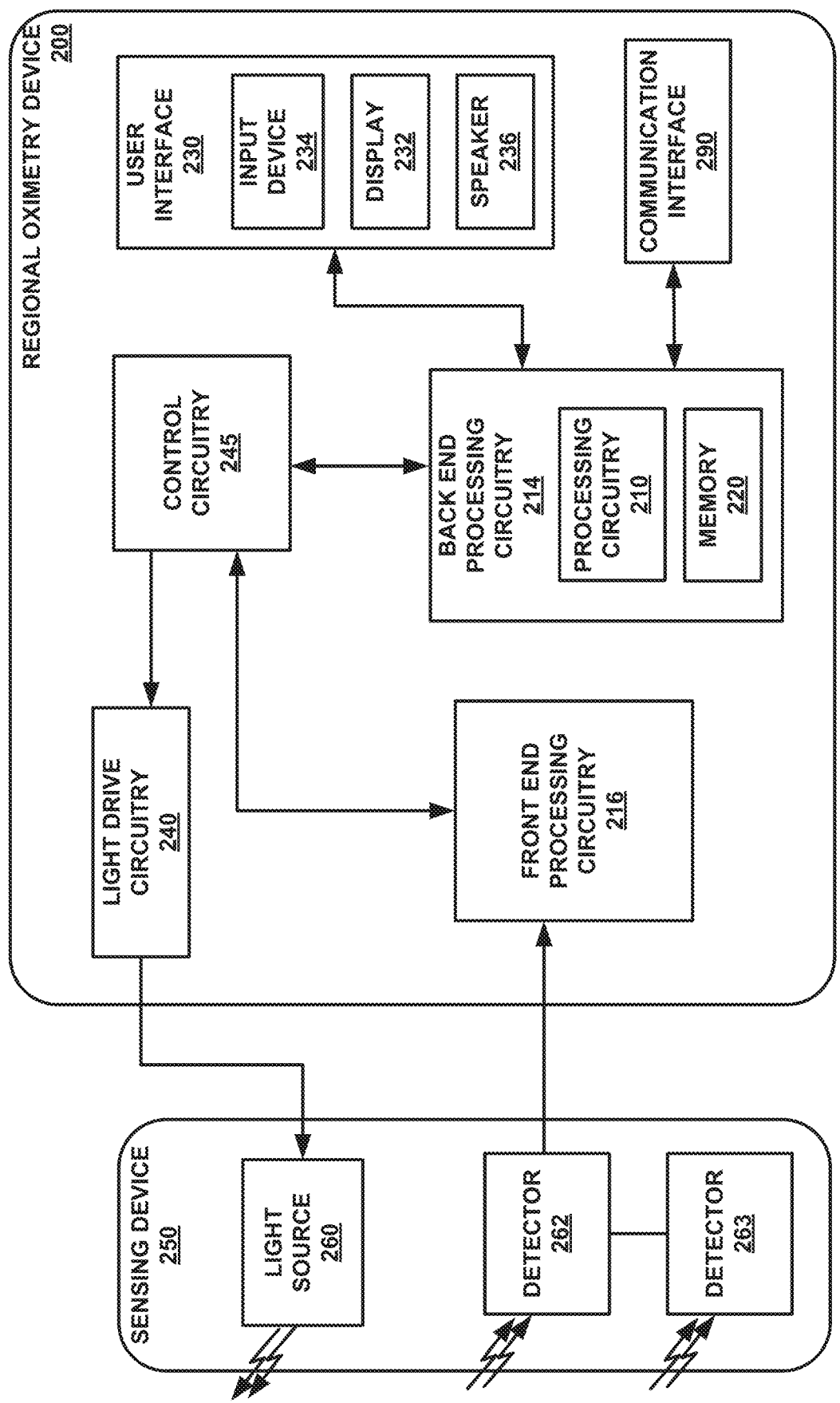
FIG. 2 is a conceptual block diagram illustrating an example regional oximetry device configured to monitor an autoregulation status of a patient.

FIG. 2 is a conceptual block diagram illustrating an example regional oximetry device 200 configured to monitor the autoregulation status of a patient. In the example shown in FIG. 2, regional oximetry device 200 is coupled to sensing device 250 and may be collectively referred to as a regional oximetry system, which each generate and process physiological signals of a subject. In some examples, sensing device 250 and regional oximetry device 200 may be part of an oximeter. As shown in FIG. 2, regional oximetry device 200 includes back-end processing circuitry 214, user interface 230, light drive circuitry 240, front-end processing circuitry 216, control circuitry 245, and communication interface 290. Regional oximetry device 200 may be communicatively coupled to sensing device 250. Regional oximetry device 200 is an example of regional oximetry device 100 shown in FIG. 1. In some examples, regional oximetry device 200 may also include a blood pressure sensor and/or a blood volume sensor (e.g., sensing devices 151 and 152 of FIG. 1).

In the example shown in FIG. 2, sensing device 250 includes light source 260, detector 262, and detector 263. In some examples, sensing device 250 may include more than two detectors. Light source 260 may be configured to emit photonic signals having two or more wavelengths (e.g., up to four or more wavelengths) of light (e.g., red and infrared (IR)) into a subject's tissue. For example, light source 260 may include a red light emitting light source and an IR light emitting light source, (e.g., red and IR LEDs), for emitting light into the tissue of a subject to generate physiological signals. In some examples, the red wavelength may be between about 600 nm and about 700 nm, and the IR wavelength may be between about 800 nm and about 1000 nm. Other wavelengths of light may be used in other examples. Light source 260 may include any number of light sources with any suitable characteristics. In examples in which an array of sensors is used in place of sensing device 250, each sensing device may be configured to emit a single wavelength. For example, a first sensing device may emit only a red light while a second sensing device may emit only an IR light. In some examples, light source 260 may be configured to emit two or more wavelengths of near-infrared light (e.g., wavelengths between 600 nm and 1000 nm) into a subject's tissue. In some examples, light source 260 may be configured to emit four wavelengths of light (e.g., 724 nm, 770 nm, 810 nm, and 850 nm) into a subject's tissue. In some examples, the subject may be a medical patient.

As used herein, the term "light" may refer to energy produced by radiative sources and may include one or more of ultrasound, radio, microwave, millimeter wave, infrared, visible, ultraviolet, gamma ray or X-ray electromagnetic radiation. Light may also include any wavelength within the radio, microwave, infrared, visible, ultraviolet, or X-ray spectra, and that any suitable wavelength of electromagnetic radiation may be appropriate for use with the present techniques. Detectors 262 and 263 may be chosen to be specifically sensitive to the chosen targeted energy spectrum of light source 260.

In some examples, detectors 262 and 263 may be configured to detect the intensity of multiple wavelengths of near-infrared light. In some examples, detectors 262 and 263 may be configured to detect the intensity of light at the red and IR wavelengths. In some examples, an array of detectors may be used and each detector in the array may be configured to detect an intensity of a single wavelength. In operation, light may enter detector 262 after passing through the subject's tissue, including skin, bone, and other shallow tissue (e.g., non-cerebral tissue and shallow cerebral tissue). Light may enter detector 263 after passing through the subject's tissue, including skin, bone, other shallow tissue (e.g., non-cerebral tissue and shallow cerebral tissue), and deep tissue (e.g., deep cerebral tissue). Detectors 262 and 263 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detectors 262 and 263.

After converting the received light to an electrical signal, detectors 262 and 263 may send the detection signals to regional oximetry device 200, which may process the detection signals and determine physiological parameters (e.g., based on the absorption of the red and IR wavelengths in the subject's tissue at both detectors). In some examples, one or more of the detection signals may be preprocessed by sensing device 250 before being transmitted to regional oximetry device 200. Additional example details of determining oxygen saturation based on light signals may be found in commonly assigned U.S. Pat. No. 9,861,317, which issued on Jan. 9, 2018, and is entitled "Methods and Systems for Determining Regional Blood Oxygen Saturation," the entire content of which is incorporated herein by reference.

Control circuitry 245 may be coupled to light drive circuitry 240, front-end processing circuitry 216, and back-end processing circuitry 214, and may be configured to control the operation of these components. In some examples, control circuitry 245 may be configured to provide timing control signals to coordinate their operation. For example, light drive circuitry 240 may generate one or more light drive signals, which may be used to turn on and off light source 260, based on the timing control signals provided by control circuitry 245. Front-end processing circuitry 216 may use the timing control signals to operate synchronously with light drive circuitry 240. For example, front-end processing circuitry 216 may synchronize the operation of an analog-to-digital converter and a demultiplexer with the light drive signal based on the timing control signals. In addition, the back-end processing circuitry 214 may use the timing control signals to coordinate its operation with front-end processing circuitry 216.

Light drive circuitry 240, as discussed above, may be configured to generate a light drive signal that is provided to light source 260 of sensing device 250. The light drive signal may, for example, control the intensity of light source 260 and the timing of when light source 260 is turned on and off. In some examples, light drive circuitry 240 provides one or more light drive signals to light source 260. Where light source 260 is configured to emit two or more wavelengths of light, the light drive signal may be configured to control the operation of each wavelength of light. The light drive signal may comprise a single signal or may comprise multiple signals (e.g., one signal for each wavelength of light).

Front-end processing circuitry 216 may perform any suitable analog conditioning of the detector signals. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. The conditioned analog signals may be processed by an analog-to-digital converter of circuitry 216, which may convert the conditioned analog signals into digital signals. Front-end processing circuitry 216 may operate on the analog or digital form of the detector signals to separate out different components of the signals. Front-end processing circuitry 216 may also perform any suitable digital conditioning of the detector signals, such as low pass, high pass, band pass, notch, averaging, or any other suitable filtering, amplifying, performing an operation on the signal, performing any other suitable digital conditioning, or any combination thereof. Front-end processing circuitry 216 may decrease the number of samples in the digital detector signals. In some examples, front-end processing circuitry 216 may also remove dark or ambient contributions to the received signal.

Back-end processing circuitry 214 may include processing circuitry 210 and memory 220. Processing circuitry 210 may include an assembly of analog or digital electronic components and may be configured to execute software, which may include an operating system and one or more applications, as part of performing the functions described herein with respect to, e.g., processing circuitry 110 of FIG. 1. Processing circuitry 210 may receive and further process physiological signals received from front-end processing circuitry 216. For example, processing circuitry 210 may determine one or more physiological parameter values based on the received physiological signals. For example, processing circuitry 210 may compute one or more of regional oxygen saturation, blood oxygen saturation (e.g., arterial, venous, or both), pulse rate, respiration rate, respiration effort, blood pressure, hemoglobin concentration (e.g., oxygenated, deoxygenated, and/or total), any other suitable physiological parameters, or any combination thereof.

Processing circuitry 210 may perform any suitable signal processing of a signal, such as any suitable band-pass filtering, adaptive filtering, closed-loop filtering, any other suitable filtering, and/or any combination thereof. Processing circuitry 210 may also receive input signals from additional sources not shown. For example, processing circuitry 210 may receive an input signal containing information about treatments provided to the subject from user interface 230. Additional input signals may be used by processing circuitry 210 in any of the determinations or operations it performs in accordance with back-end processing circuitry 214 or regional oximetry device 200.

Processing circuitry 210 is an example of processing circuitry 110 and is configured to perform the techniques of this disclosure. For example, processing circuitry 210 is configured to receive signals indicative of physiological parameters. Processing circuitry 210 is also configured to determine a cerebral autoregulation status based on measured blood pressures and/or adjusted measured blood pressures due to a detected abrupt change in the measured blood pressures.

Memory 220 may include any suitable computer-readable media capable of storing information that can be interpreted by processing circuitry 210. In some examples, memory 220 may store reference absorption curves, reference sets, determined values, such as blood oxygen saturation, pulse rate, blood pressure, fiducial point locations or characteristics, initialization parameters, any other determined values, or any combination thereof, in a memory device for later retrieval. Memory 220 may also store thresholds for detecting abrupt changes in blood pressure, and so on. Back-end processing circuitry 214 may be communicatively coupled with user interface 230 and communication interface 290.

User interface 230 may include input device 234, display 232, and speaker 236 in some examples. User interface 230 is an example of user interface 130 shown in FIG. 1, and display 232 is an example of display 132 shown in FIG. 1. User interface 230 may include, for example, any suitable device such as one or more medical devices (e.g., a medical monitor that displays various physiological parameters, a medical alarm, or any other suitable medical device that either displays physiological parameters or uses the output of back-end processing 214 as an input), one or more display devices (e.g., monitor, personal digital assistant (PDA), mobile phone, tablet computer, clinician workstation, any other suitable display device, or any combination thereof), one or more audio devices, one or more memory devices, one or more printing devices, any other suitable output device, or any combination thereof.

Input device 234 may include one or more of any type of user input device such as a keyboard, a mouse, a touch screen, buttons, switches, a microphone, a joystick, a touch pad, or any other suitable input device or combination of input devices. In other examples, input device 234 may be a pressure-sensitive or presence-sensitive display that is included as part of display 232. Input device 234 may also receive inputs to select a model number of sensing device 250, blood pressure sensor 250 (FIG. 2), or blood pressure processing equipment. In some examples, processing circuitry 210 may determine the type of presentation for display 232 based on user inputs received by input device 234. For example, processing circuitry 210 may be configured to present, via display 232, graphical user interface 300 shown in FIG. 3 or graph 400 shown in FIG. 4.

Figure 3:
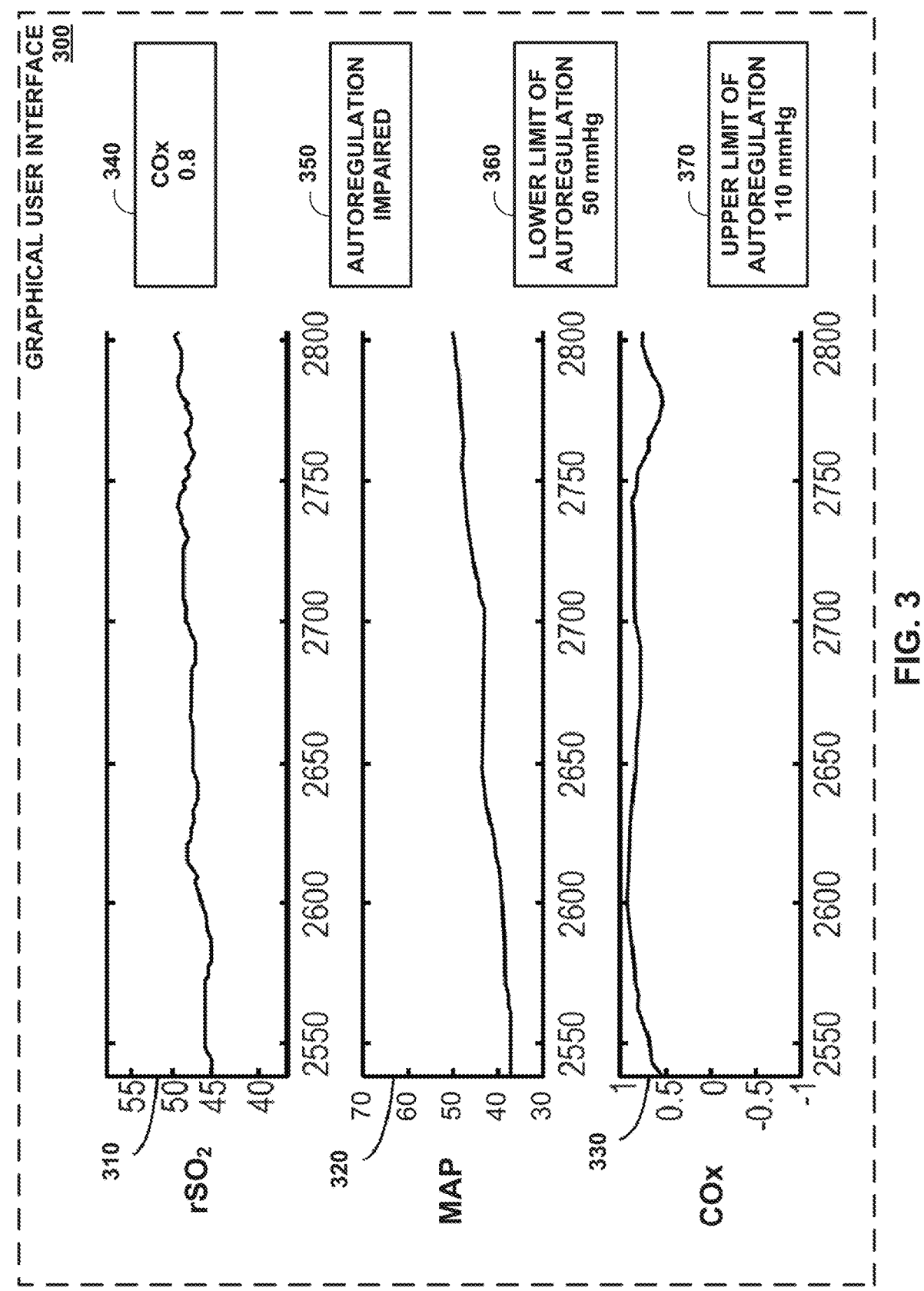
FIG. 3 illustrates an example graphical user interface including autoregulation information presented on a display.

In some examples, the subject may be a medical patient and display 232 may exhibit a list of values which may generally apply to the subject, such as, for example, an oxygen saturation signal indicator, a blood pressure signal indicator, a COx signal indicator, a COx value indicator, and/or an autoregulation status indicator. Display 232 may also be configured to present additional physiological parameter information. Graphical user interface 300 shown in FIG. 3 is an example of an interface that can be presented via display 232 of FIG. 2 under the control of processing circuitry 210. Additionally, display 232 may present, for example, one or more estimates of a subject's regional oxygen saturation generated by regional oximetry device 200 (referred to as an "$rSO_2$" measurement). Display 232 may also present indications of the upper and lower limits of cerebral autoregulation. In some examples, user interface 230 includes speaker 236 that is configured to generate and provide an audible sound that may be used in various examples, such as for example, sounding an audible notification in the event that a patient's physiological parameters are not within a predefined normal range and/or in the event that processing circuitry 210 determines that sensed blood pressure values may be inaccurate due to a non-physiological reason such as due to movement of a blood pressure probe of blood pressure sensor 151 (FIG. 1).

Communication interface 290 may enable regional oximetry device 200 to exchange information with other external or implanted devices. Communication interface 290 may include any suitable hardware, software, or both, which may allow regional oximetry device 200 to communicate with electronic circuitry, a device, a network, a server or other workstations, a display, or any combination thereof. For example, regional oximetry device 200 may receive MAP (or other measured blood pressure) values and/or oxygen saturation values from an external device via communication interface 290.

The components of regional oximetry device 200 that are shown and described as separate components are shown and described as such for illustrative purposes only. In some examples the functionality of some of the components may be combined in a single component. For example, the functionality of front end processing circuitry 216 and back-end processing circuitry 214 may be combined in a single processor system. Additionally, in some examples the functionality of some of the components of regional oximetry device 200 shown and described herein may be divided over multiple components. For example, some or all of the functionality of control circuitry 245 may be performed in front end processing circuitry 216, in back-end processing circuitry 214, or both. In other examples, the functionality of one or more of the components may be performed in a different order or may not be required. In some examples, all of the components of regional oximetry device 200 can be realized in processor circuitry.

FIG. 3 illustrates an example graphical user interface 300 including autoregulation information presented on a display. FIG. 3 is an example of a presentation by processing circuitry 110 on display 132 shown in FIG. 1 or by processing circuitry 210 on display 232 shown in FIG. 2. Although FIGS. 3-8 are described with respect to processing circuitry 110 of regional oximetry device 100 (FIG. 1), in other examples, processing circuitry 210, 214, and/or 216 (FIG. 2), alone or in combination with processing circuitry 110, may perform any part of the techniques of FIGS. 3-8.

Graphical user interface 300 may be configured to display various information related to blood pressure, oxygen saturation, the COx index, limits of cerebral autoregulation, and/or cerebral autoregulation status. As shown, graphical user interface 300 may include oxygen saturation signal indicator 310, blood pressure signal indicator 320, and COx signal indicator 330. Graphical user interface 300 may include COx value indicator 340, autoregulation status indicator 350, and limit of autoregulation indicators 360 and 370.

Blood pressure signal indicator 320 may present a set of MAP values determined by processing circuitry 110 of regional oximetry device 100. The MAP values may be based on measured blood pressure values, but the raw measured blood pressure values (e.g., showing intra-cardia cycle variations) may be displayed in other examples. In some examples, blood pressure signal indicator 320 may present MAP values as discrete points over time or in a table. Blood pressure signal indicator 320 may also present MAP values as a moving average or waveform of discrete points. Blood pressure signal indicator 320 may present MAP values as a single value (e.g., a number) representing a current MAP value. Oxygen saturation signal indicator 310 and COx signal indicator 330 may also present $rSO_2$ values and COx values, respectively, as discrete points, in a table, as a moving average, as a waveform, and/or as a single value. In other examples, the data from two or more of oxygen saturation signal indicator 310, blood pressure signal indicator 320, or COx signal indicator 330 may be combined together on a single graph.

COx signal indicator 330 may present a set of correlation coefficients determined by processing circuitry 110. Processing circuitry 110 may determine the correlation coefficients as a function of the oxygen saturation values presented in oxygen saturation signal indicator 310 and the MAP values presented in blood pressure signal indicator 320. In some examples, a COx value at or near one indicates the cerebral autoregulation status of a patient is impaired, as shown in autoregulation status indicator 350.

COx value indicator 340 shows a COx value determined by processing circuitry 110, which is shown as 0.8 in the example of FIG. 3 and may change over time. The COx value of 0.8 may result in a determination by processing circuitry 110 that the cerebral autoregulation status of the patient is impaired. Processing circuitry 110 may be configured to present, as the COx value in COx value indicator 340, the most recently determined COx value. In order to determine the cerebral autoregulation status of a patient for presentation in autoregulation status indicator 350, processing circuitry 110 may determine whether the most recent MAP value shown in blood pressure signal indicator 320 is between the limits of cerebral autoregulation presented in limit of autoregulation indicators 360 and 370. Processing circuitry 110 can present text such as "intact" or "impaired" in autoregulation status indicator 350. Processing circuitry 110 can also present a color such as green (e.g., for intact cerebral autoregulation) or red (e.g., for impaired cerebral autoregulation) to help aid a user's understanding of an autoregulation status of the patient.

In some examples, processing circuitry 110 may present limit of autoregulation indicators 360 and/or 370 in terms of blood pressure, for example, millimeters of mercury (mmHg). Processing circuitry 110 can determine the limits of cerebral autoregulation (LLA and ULA) for presentation in indicators 360 and 370 based on a relationship between the blood pressure of a patient and another physiological parameter of the patient. For example, indicator 360 may be highlighted when the LLA has been exceeded or indicator 360 may be highlighted when the ULA has been exceeded. In other examples, a single indicator may present the type of limit that has been exceed by the MAP value. If the LLA or ULA change, processing circuitry 110 may control user interface 300 to change the value of the LLA or ULA in accordance with any change to that respective value.

In some examples, processing circuitry 110 determines the cerebral autoregulation status for presentation in autoregulation status indicator 350 by comparing the most recently determined MAP value to the limits of cerebral autoregulation. For example, if processing circuitry 110 estimates the LLA at 50 mmHg and determines a MAP value at 40 mmHg, then processing circuitry 110 may determine that the cerebral autoregulation status of the patient is impaired, or not intact. In response to determining that the MAP value is less than or equal to the estimate of the LLA for more than the predetermined period of time, processing circuitry 110 may output a notification in autoregulation status indicator 350 as text, color, blinking, and/or any other suitable visible or audible manner.

Figure 4:
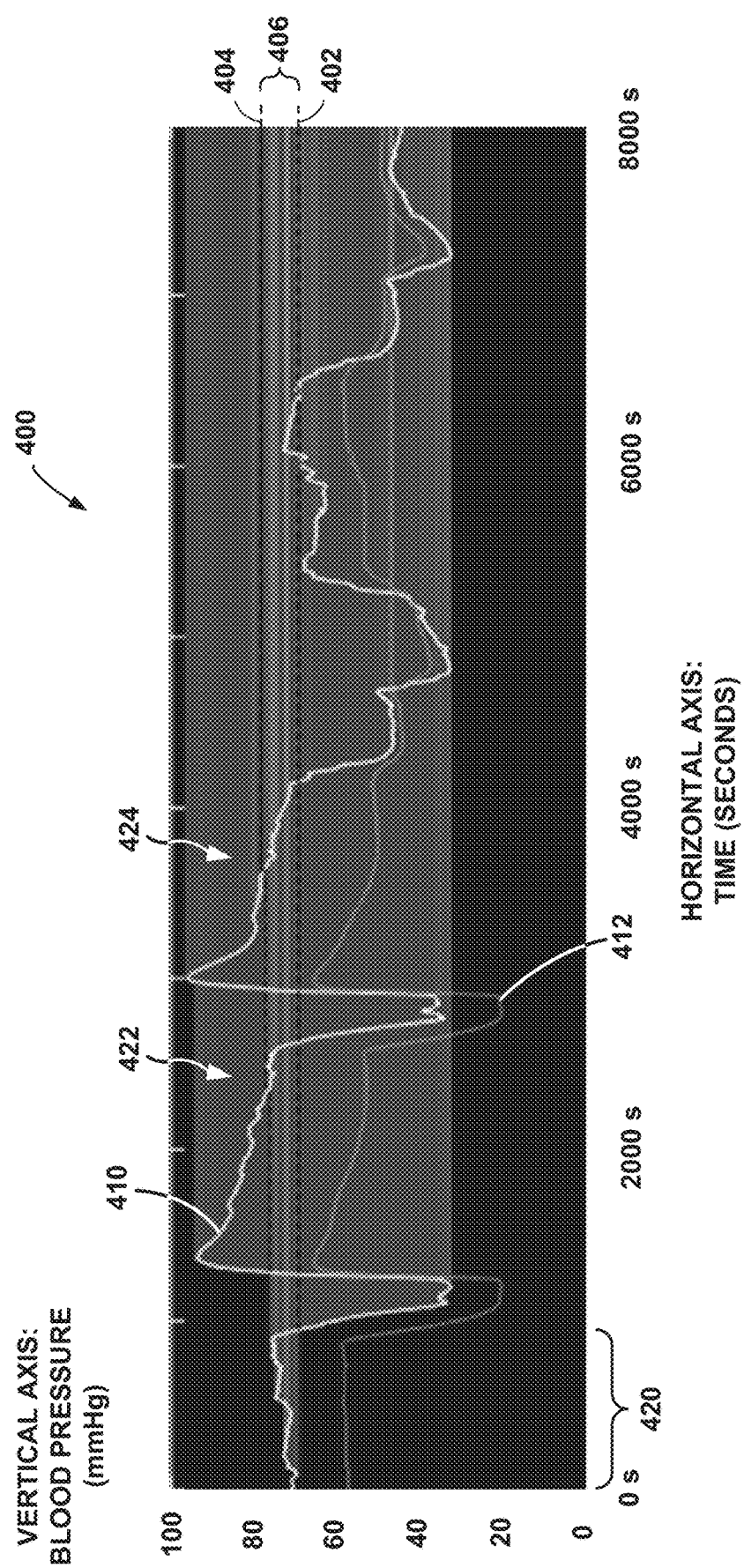
FIG. 4 is a graph illustrating blood pressure over time along with the lower and upper limits of autoregulation, in accordance with some examples of this disclosure.

FIG. 4 is a graph 400 illustrating blood pressure over time along with the lower and upper limits of cerebral autoregulation 402 and 404 (e.g., LLA 402 and ULA 404). Graph 400 is an example of a presentation of limits of cerebral autoregulation 402 and 404 and a cerebral autoregulation status by processing circuitry 110 or 214 via display 132 or 232. Processing circuitry 110 can also present graph 400 on, e.g., graphical user interface 300.

Processing circuitry 110 can generate and present graph 400 to show blood pressure line 410 of a patient over time, along with the estimates of the limits of cerebral autoregulation 402 and 404. Processing circuitry 110 can also generate oxygen saturation line 412 of the patient over time. Processing circuitry 110 can also present an indication of cerebral autoregulation status in graph 400 by, for example, presenting blood pressure line 410 between or outside of LLA 402 and ULA 404. Intact area of cerebral autoregulation 406 exists between LLA 402 and ULA 404. While FIG. 4 does not show any abrupt changes to blood pressure due to pressure probe movement, processing circuitry 110 could generate graph 440 to show such an issue could be shown if it were to occur.

In some examples, processing circuitry 110 is configured to present intact area of cerebral autoregulation 406 between LLA 402 and ULA 404 as a green color (e.g., an intact region of cerebral autoregulation) or another color. Processing circuitry 110 can also present the region of graph 400 above ULA 404 and the region below LLA 402 as red colors (e.g., impaired regions of cerebral autoregulation) or another color other than the color used for intact area 406 which may or may not be different shades of red, for example.

In some examples, processing circuitry 110 is configured to present an indication of the cerebral autoregulation status as a color, such as green or red. Processing circuitry 110 may present the color on a graphical user interface such as graph 400 or graphical user interface 300 shown in FIG. 3. Processing circuitry 110 may be configured to change the intensity of the color(s) in response to determining a change in a limit of cerebral autoregulation. Processing circuitry 110 can change the intensity of the color based on the magnitude of the determined change in the limit of cerebral autoregulation. For example, in response to determining a relatively large change in a limit of cerebral autoregulation, processing circuitry 110 may significantly reduce the intensity of the green color presented in intact area of cerebral autoregulation 406. The less intense green color may indicate lower confidence in the estimates of limits of cerebral autoregulation 402 and 404.

In response to determining a relatively small change in the limit of cerebral autoregulation, processing circuitry 110 may slightly reduce the intensity of the green color presented in intact area of cerebral autoregulation 406. In response to determining no change in the limit of cerebral autoregulation, processing circuitry 110 may not change or may increase the intensity of the green color presented in intact area of cerebral autoregulation 406. Thus, with respect to intact area of cerebral autoregulation 406, a large change may result in a much dimmer green color, a small change may result in a slightly dimmer green color, and no change may result in a brighter green color or no change in the green color. Processing circuitry 110 may use similar techniques to change the red color in the impaired areas of cerebral autoregulation in graph 400. In addition, similar changes in color may be provided in response to processing circuitry 110 detecting abrupt changes to the measured blood pressure, however, other colors may be used to indicate that the change to blood pressure and/or LLA and ULA are due to external factors instead of an actual physiological change with the patient.

In response to determining a change in the cerebral autoregulation of a patient, processing circuitry 110 may change the intensity of the colors for previous times in graph 400. For example, processing circuitry 110 can make the colors for times before the determined change in cerebral autoregulation less intense. Processing circuitry 110 may use the normal or default color intensity for times after the determined change. In response to determining a change in cerebral autoregulation at 4,000 seconds on graph 400, processing circuitry 110 can dim the green and red colors for times before 4,000 seconds and use the normal intensity for colors after 4,000 seconds. The dim colors before the determined change indicate reduced confidence, and the normal color intensity after the determined change indicates a default level of confidence.

For example, at time 422 and at time 424, the line associated with ULA 404 moves upward and the area indicating intact cerebral autoregulation 406 expands in size. When processing circuitry 110 determines a change in cerebral autoregulation, processing circuitry 110 may be configured to determine the amplitude of change between a previous estimate and an updated estimate of the limit of cerebral autoregulation. At time 422, processing circuitry 110 may determine that the upper limit of cerebral autoregulation has increased by two mmHg. Processing circuitry 110 may be configured to present an indication of the amplitude of change in the limit of cerebral autoregulation in response to determining the amplitude of change between the previous estimate and the updated estimate. Processing circuitry 110 may present, via display 132, text such as "upper limit +2 mmHg".

Graph 400 depicts LLA 402 and ULA 404 at approximately 68 and 75 mmHg, respectively. In response to determining that blood pressure line 410 has a value between 68 and 75 mmHg, processing circuitry 110 may present an indication of an intact cerebral autoregulation status, such as blood pressure line 410 within an area of green color between LLA 402 and ULA 404. Processing circuitry 110 may also present an indication of the intact cerebral autoregulation status such as text (e.g., "autoregulation: intact").

Time period 420 (e.g., the first eight hundred seconds) does not include an indication of LLA 402 or ULA 404 because processing circuitry 110 may not yet have obtained sufficient data to determine LLA 402 or ULA 404. When blood pressure line 410 drops below 60 mmHg, processing circuitry 110 may determine and present LLA 402 on graph 400. When blood pressure line 410 increases above 80 mmHg, processing circuitry 110 may determine and present ULA 404 on graph 400.

FIG. 5 includes graph 510 illustrating an example blood pressure, LLA, and ULA when blood pressure is adjusted to compensate for an abrupt change in measured blood pressure. Graph 510 is an example graphical user interface that may be displayed by processing circuitry, e.g., processing circuitry 110 via display 132 (FIG. 1). As shown in FIG. 5, measured blood pressure is represented by initial blood pressure trace 516A and updated blood pressure trace 516B (collectively "blood pressure 516"). First ULA values 512A and second ULA values 512B (collectively "ULA values 512") are shown in conjunction with first LLA values 514A and second ULA values 514B (collectively "LLA values 514").

In the example of FIG. 5, initial blood pressure trace 516A indicates the measured blood pressures over time, e.g., sensed by blood pressure sensor 151 in FIG. 1 via a probe introduced into an artery of a patient. Processing circuitry 110 determines first ULA values 512A and first LLA values 514A on the blood pressures of the initial blood pressure trace 516A to provide the limits of the intact autoregulation zone. At time T, processing circuitry 110 may detect an abrupt change in the measured blood pressure from pressure value 520 to lower pressure value 522. The difference value between pressure value 520 and pressure value 522 is represented by magnitude A, and processing circuitry 110 may determine that an abrupt change in pressure occurred because magnitude A is greater than or equal to a threshold value.

In response to determining that magnitude A is greater than or equal to the threshold value, processing circuitry 110 generates an offset value that compensates for the change in blood pressure and applies the offset value to pressure value 522 and subsequently measured blood pressure values (after time T) to generate updated blood pressure trace 516B. Since processing circuitry 110 has compensated for the movement to the pressure probe by applying the offset value to the blood pressure values measured using the probe, processing circuitry 110 may continue to determine the ULA values 512B and LLA values 514B based on the previous blood pressures of initial blood pressure trace 516A and the updated blood pressure values of updated blood pressure trace 516B.

In some examples, the threshold value that triggers compensation for the measured blood pressure may generally be selected in a range from approximately 5 mmHg through 40 mmHg. Example threshold value may be 5, 10, 15, 20, 25, 30, 35, or 40 mmHg. However, other examples within these ranges or outside of these ranges may be used in other examples. In some examples, the threshold value that triggers compensation for the measured blood pressure may be a rate of change in the measured blood pressure selected in a range from approximately 5 mmHg/s through 20 mmHg/s. For example, example threshold values for the rate of change in the blood pressure may be 5, 10, 15, or 20 mmHg. However, other examples, may use other threshold values for the rate of change that may be indicative of an abrupt change in the measured blood pressure.

Although processing circuitry 110 may have compensated for the movement of the pressure prove to continue monitoring the autoregulation status of the patient as if the movement did not occur, it may be beneficial for the user to be informed of the detected movement to the pressure probe or other issue. For example, processing circuitry 110 may be configured to, in response to determining that the blood pressure exceeds the threshold value, control user interface 130 to present a warning that indicates that an abrupt change to the blood pressure was detected. This warning may include text, a symbol, an audible sound, or other type of warning. In some examples, the warning may indicate that a blood pressure anomaly was detected due to the specific issue, such as movement of the pressure probe within the patient. As shown in FIG. 5, this warning may be presented as at least one of the dotted lines of first ULA values 512A, first LLA values 514A, and initial blood pressure trace 516A, which change to solid lines after time T. In other words, the user may be notified by way of a change in the type of line for at least one of first ULA values 512A, first LLA values 514A, and initial blood pressure trace 516A or a change from the type of line of at least one of first ULA values 512A, first LLA values 514A, and initial blood pressure trace 516A to second ULA values 512B, second LLA values 514B, and initial blood pressure trace 516B, respectively, that device 100 has detected an abrupt change in the measured blood pressure and taken steps to compensate for that change in measured blood pressure.

In some examples, after time T, processing circuitry 110 may display the autoregulation information provided by first ULA values 512A, first LLA values 514A, and initial blood pressure trace 516A in greyscale (or another color scheme) while second ULA values 512B, second LLA values 514B, and initial blood pressure trace 516B are displayed in one or more colors different than the greyscale (or other color scheme) to differentiate between the pre-change and post-change autoregulation information.

Pressure values 520 and 522 are shown to represent the actual pressure values measured by device 100. In some examples, processing circuitry 110 may display and flag these pressure values 520 and 522 on graph 510. In other examples, processing circuitry 110 may not show pressure values 520 and 522 separately from the respective traces to which each belongs pre- and post-abrupt change in blood pressure at time T.

Although FIG. 5 illustrates only a single abrupt change to blood pressure, in some cases, processing circuitry 110 may detect two or more abrupt changes in blood pressure over time, and compensate for each of the abrupt changes when generating the information provided via graph 510. In some examples, any data shown prior to the most recent detected abrupt change in measured blood pressure may be represented as the same type of line, the same color, or otherwise not have any other distinguishing features even though a prior abrupt change may have been detected and compensated for within this data. However, graph 510 may still include an arrow or other indication for where prior abrupt changes to the measured blood pressure occurred. In other examples, the data for each period of time between consecutive abrupt changes in blood pressure may be displayed with respective types of lines or colors such that the user can easily identify each section of graph 510 that was not interrupted by an abrupt change to the measured blood pressure.

Figure 6:
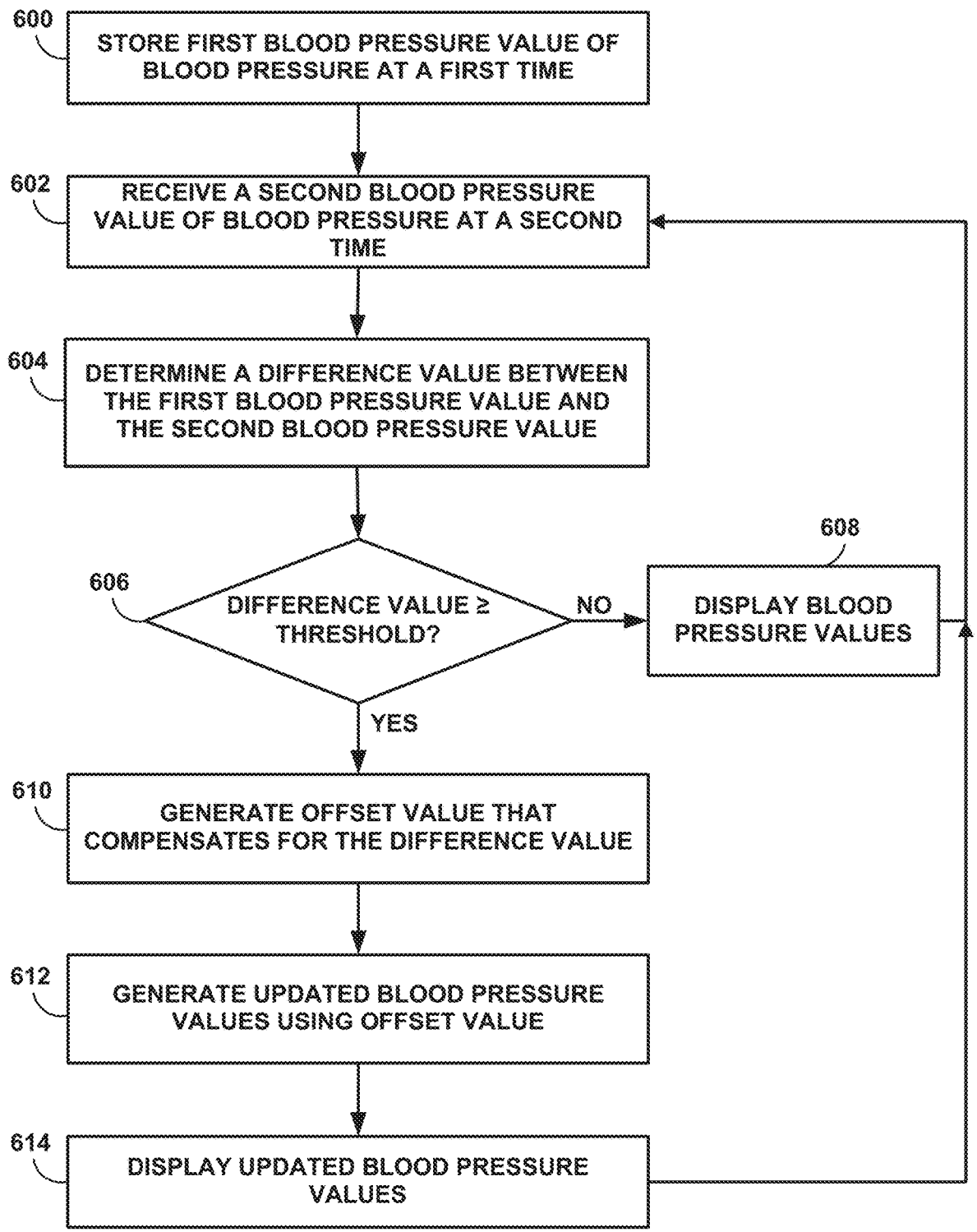
FIG. 6 is a flow diagram illustrating an example technique for compensating for an abrupt change in measured blood pressure, e.g., as shown in FIG. 5.

FIG. 6 is a flow diagram illustrating an example technique for compensating for an abrupt change in measured blood pressure as shown in FIG. 5. Although FIG. 6 (as well as FIGS. 5, 7, and 9) is described with respect to regional oximetry device 100 (FIG. 1), in other examples, the techniques described herein may be performed with other devices. For example, processing circuitry 210, 214, and/or 216 (FIG. 2), alone or in combination with processing circuitry 110 of device 100, may perform any part of the techniques of FIG. 6.

In the example of FIG. 6, processing circuitry 110 receives and stores a first blood pressure value representative of the blood pressure of a patient sensed by a blood pressure sensor (e.g., sensor 151) at a first time (600). The blood pressure may be a mean arterial pressure (MAP) or a raw blood pressure that has not been averaged or otherwise weighted based on other blood pressures, as some examples. Processing circuitry 110 then receives a second blood pressure value representative of the blood pressure of the patient sensed by the blood pressure sensor at a second time after the first time (602). Processing circuitry 110 then determines a difference value between the first blood pressure value and the second blood pressure value (604).

Processing circuitry 110 compares the difference value to a threshold value (606). In some examples, the different value may be a pressure value that is compared against another pressure threshold value. In other examples, the difference value may be computed to be rate of change in the blood pressure between the first and second blood pressure values, wherein the rate of change is then compared to a threshold rate of change. Other types of comparisons can be made that identify whether or not the change in blood pressure is significant and/or indicative of a non-physiological event such as the pressure probe moving to a different location within the blood vessel.

If the different value is not greater than or equal to the threshold ("NO" branch of block 606), then processing circuitry 110 controls display device 132 to display the measured blood pressures (608) and receive another blood pressure value (602). If the different value is greater than or equal to the threshold ("YES" branch of block 606), then processing circuitry 110 generates an offset value that compensates for the difference value (610). For example, the offset value may be an additive inverse of the difference value. Processing circuitry 110 than generates updated blood pressure values based on the offset value. For example, processing circuitry 110 may add the offset value to the second blood pressure value and subsequently received blood pressures (after the second time) to compensate for the new location of the pressure probe (612). Processing circuitry 110 the controls display device 132 to display the updated blood pressure values, e.g., similar to the updated blood pressure trace 516B shown in FIG. 5 (614).

In other examples of the process described in FIG. 6, one or more steps may be rearranged, combined, performed in parallel, or even removed. For example, processing circuitry 110 may receive the next blood pressure value during or between any the execution of blocks 604 through 614. The process of FIG. 6 may also include additional features. For example, processing circuitry 110 may determine LLA and ULA values based on the initial and updated blood pressure values. In other examples, processing circuitry 110 may control the display device to change type of lines or color of lines for blood pressure values, LLA values, and/or ULA values if the difference value exceeds the threshold, as described herein.

FIG. 7 includes graph 710 illustrating an example blood pressure, LLA, and ULA when the LLA and ULA are adjusted to compensate for an abrupt change in measured blood pressure. Graph 710 is an example of a graphical user interface that processing circuitry 110 (or other processing circuitry) may generate and display via display device 132. As shown in FIG. 7, measured blood pressure is represented by initial blood pressure trace 716A and updated blood pressure trace 716B (collectively "blood pressure trace 716"). FIG. 7 is similar to FIG. 5, but in FIG. 7 the ULA and LLA values are adjusted due to the abrupt change in blood pressure instead of the blood pressure values themselves. In some examples, the thresholds and display features may be similar to those described with respect to FIG. 5. First ULA values 712A and second ULA values 712B (collectively "ULA values 712") are shown in conjunction with first LLA values 714A and second ULA values 714B (collectively "LLA values 714").

In the example of FIG. 7, initial blood pressure trace 716A indicates the measured blood pressures over time. Processing circuitry 110 determines first ULA values 712A and first LLA values 714A based on the blood pressures of the initial blood pressure trace 716A to provide the limits of the intact autoregulation zone. At time T, processing circuitry 110 may detect an abrupt change in the measured blood pressure from pressure value 720 to lower pressure value 722. The difference value between pressure value 720 and pressure value 722 is represented by magnitude B, and processing circuitry 110 may determine that an abrupt change in pressure occurred because magnitude B is greater than a predetermined threshold value.

In response to determining that magnitude B is greater than or equal to the threshold value, processing circuitry 110 generates an offset value that compensates for the change in blood pressure and applies the offset value to ULA and LLA values to generate ULA values 712B and LLA values 714B. For example, since the blood pressure values of blood pressure trace 716B are now lower by magnitude B with respect to blood pressure trace 716A, the ULA and LLA values are similarly shifted lower. In this manner, processing circuitry 110 can continue to monitor the autoregulation status of the patient without changing the measured blood pressure values. Processing circuitry 110 may then also determine ULA and LLA values after time T using the actual measured blood pressure values. In some examples, processing circuitry 110 may downweight or otherwise reduce the significance of blood pressures received prior to time T when determining ULA values 712B and LLA values 714B in order to minimize the effect of pre-change blood pressures to current ULA and LLA values.

In some examples, the threshold value that triggers compensation for the measured blood pressure may generally be selected in a range from approximately 5 mmHg through 40 mmHg. Example threshold value may be 5, 10, 15, 20, 25, 30, 35, or 40 mmHg. However, other examples within these ranges or outside of these ranges may be used in other examples. In some examples, the threshold value that triggers compensation for the measured blood pressure may be a rate of change in the measured blood pressure selected in a range from approximately 5 mmHg/s through 20 mmHg/s. For example, example threshold values for the rate of change in the blood pressure may be 5, 10, 15, or 20 mmHg. However, other examples, may use other threshold values for the rate of change that may be indicative of an abrupt change in the measured blood pressure.

Although processing circuitry 110 may have compensated for the movement of the pressure probe of sensor 151 to continue monitoring the autoregulation status of the patient as if the movement did not occur, it may be beneficial for the user to be informed of the detected movement to the pressure probe or other issue. For example, processing circuitry 110 may be configured to, in response to determining that the blood pressure is greater than or equal to the threshold value, control user interface 130 to present a notification that indicates that an abrupt change to the blood pressure was detected. This warning may include text, a symbol, an audible sound, or other type of warning. In some examples, the warning may indicate that a blood pressure anomaly was detected due to the specific issue, such as movement of the pressure probe within the patient.

As shown in FIG. 7, this warning may be presented as at least one of the dotted lines of first ULA values 712A, first LLA values 714A, and initial blood pressure trace 716A, which change to solid lines after time T. In other words, the user may be notified by way of a change in the type of line for at least one of first ULA values 712A, first LLA values 714A, and initial blood pressure trace 716A or a change from the type of line of at least one of first ULA values 712A, first LLA values 714A, and initial blood pressure trace 716A to second ULA values 712B, second LLA values 714B, and initial blood pressure trace 716B, respectively, that device 100 has detected an abrupt change in the measured blood pressure and taken steps to compensate for that change in second ULA values 712B and second LLA values 714B. In some examples, the autoregulation information of first ULA values 712A, first LLA values 714A, and initial blood pressure trace 716A may be displayed in greyscale (or another color scheme) while second ULA values 712B, second LLA values 714B, and initial blood pressure trace 716B are displayed in one or more colors different than the greyscale (or other color scheme used for the time before time T) to differentiate between the pre-abrupt change and post-abrupt change autoregulation information.

Pressure values 720 and 722 are shown to represent the actual pressure values measured by the system. In some examples, these pressure values 720 and 722 may be displayed on graph 710. In other examples, pressure values 720 and 722 may not be shown separately from the respective traces to which each belongs pre- and post-change in blood pressure.

Although FIG. 7 illustrates only a single abrupt change to blood pressure, in some examples, processing circuitry 110 may detect, compensate for, and display on graph 710 two or more abrupt changes in blood pressure. In some examples, processor 110 may represent any data generated prior to the most recent detected abrupt change in measured blood pressure as the same type of line, the same color, or otherwise not have any other distinguishing features even though a prior abrupt change may have been detected and compensated for within this data. However, graph 710 may still include an arrow or other indication for where prior abrupt changes to the measured blood pressure occurred. In other examples, processing circuitry 110 may represent the data for each period of time between consecutive abrupt changes in blood pressure with respective types of lines or colors such that the user can easily identify each section of graph 710 that was not interrupted by an abrupt change to the measured blood pressure.

Figure 8:
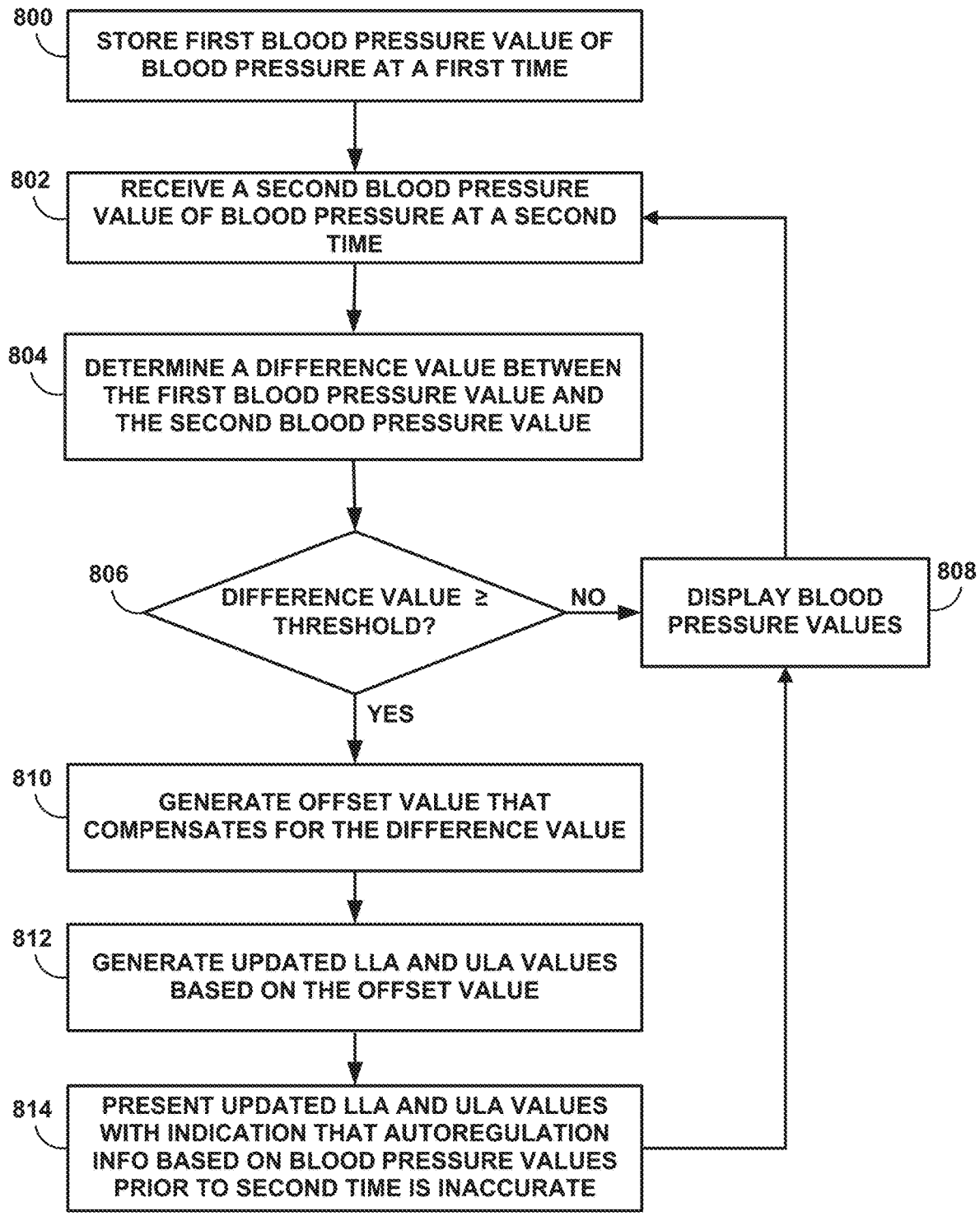
FIG. 8 is a flow diagram illustrating an example technique for compensating for an abrupt change in measured blood pressure as shown in FIG. 7.

FIG. 8 is a flow diagram illustrating an example technique for compensating for an abrupt change in measured blood pressure as shown in FIG. 7. Although FIG. 8 is described with respect to regional oximetry device 100 (FIG. 1), in other examples, other devices may perform any part of the technique of FIG. 8. For example, processing circuitry 210, 214, and/or 216 (FIG. 2), alone or in combination with processing circuitry 110, may perform any part of the technique of FIG. 8.

In the example of FIG. 8, processing circuitry 110 receives and stores a first blood pressure value representative of the blood pressure of a patient sensed by a blood pressure sensor (e.g., sensor 151) at a first time (800). The blood pressure may be a mean arterial pressure (MAP) or a raw blood pressure that has not been averaged or otherwise weighted based on other blood pressures, as some examples. Processing circuitry 110 then receives a second blood pressure value representative of the blood pressure of the patient sensed by the blood pressure sensor at a second time (802). Processing circuitry 110 then determines a difference value between the first blood pressure value and the second blood pressure value (804).

Processing circuitry 110 compares the difference value to a threshold value (806). In some examples, the different value may be a pressure value that is compared against another pressure threshold. In other examples, the difference value may be computed to be rate of change in the blood pressure between the first and second blood pressure values, wherein the rate of change is then compared to a threshold rate of change. Other types of comparisons can be made that identify whether or not the change in blood pressure is significant and/or indicative of a non-physiological event such as the pressure probe moving to a different location within the blood vessel.

If the different value is not greater than or equal to the threshold ("NO" branch of block 806), then processing circuitry 110 controls a display device to display the measured blood pressures (808) and receive another blood pressure value (802). If the different value is greater than or equal to the threshold ("YES" branch of block 806), then processing circuitry 110 generates an offset value that compensates for the difference value (810). For example, the offset value may be an additive inverse of the difference value. Processing circuitry 110 than generates updated LLA and ULA values based on the offset value (812). For example, processing circuitry 110 may add the offset value to the LLA and ULA values determined at least in part of those blood pressures measured prior to the abrupt change in the blood pressure to compensate for the new location of the pressure probe (812). Processing circuitry 110 the controls display device 132 to display the updated LLA and ULA values similar to the second ULA values 712B and second LLA values 714B shown in FIG. 7 (814).

Processing circuitry 110 may determine LLA values and ULA values based on a plurality of measured blood pressures over time, such as an entirety of the measured blood pressures, or some rolling window of measured blood pressures. As the blood pressures measured after the abrupt change continue to populate the determination of the LLA and ULA values, the offset value may be needed in a decreasing amount over time because less compensation is needed when fewer pre-change blood pressures are still used to determine the LLA and ULA. Therefore, in some examples, processing circuitry 110 may iteratively reduce the offset value applied to the LLA and ULA as more post-change blood pressure values are included in the determination of the LLA and ULA.

In some examples, the rate of reducing the offset value may be based on the length of the rolling window. For example, if the LLA and ULA values are based on the 100 most recent blood pressure values, then processing circuitry 110 may reduce the offset value by $1/100$ of the offset value each time a new blood pressure value is used to determine the LLA and ULA values because the oldest blood pressure value is now excluded from the calculation. In other examples, the reduction of the offset value may not be linear of older and newer blood pressure values are weighted differently in the calculation of LLA and ULA values or as needed in order to appropriately compensate for, or mitigate, the abrupt changes to measured blood pressure that have happened in the past.

In other examples of the process described in FIG. 8, one or more steps may be rearranged, combined, performed in parallel, or even removed. For example, processing circuitry 110 may receive the next blood pressure value during or between any the execution of blocks 804 through 814. The process of FIG. 8 may also include additional features. For example, instead of an offset value, processing circuitry 110 may generate a function that, when applied to the ULA and LLA calculation, compensates for the detected abrupt change to measured blood pressure. In other examples, processing circuitry 110 may control the display device to change type of lines or color of lines for blood pressure values, LLA values, and/or ULA values if the difference value exceeds the threshold, as described herein.

The following are examples of the description herein.

Example 1

A device comprising a memory configured to store a first blood pressure value representative of a blood pressure of a patient sensed by a blood pressure sensor at a first time; and processing circuitry configured to: receive a second blood pressure value representative of the blood pressure of the patient sensed by the blood pressure sensor at a second time; determine a difference value between the first blood pressure value and the second blood pressure value; determine that the difference value is greater than or equal to a threshold value; responsive to determining that the difference value is greater than or equal to the threshold value, generate an offset value that compensates for the difference value; generate, based on the offset value and subsequently received blood pressure values representative of the blood pressure of the patient sensed after the second time, at least one updated parameter value; and output the at least one updated parameter value.

Example 2

The device of example 1, wherein the at least one updated parameter value comprises updated blood pressure values, and wherein the processing circuitry is configured to generate the updated blood pressure values by at least applying the offset value to the second blood pressure value and the subsequently received blood pressure values representative of the blood pressure of the patient sensed after the second time.

Example 3

The device of any of examples 1 and 2, wherein the at least one updated parameter value comprises at least one of an updated lower limit of autoregulation (LLA) value or an updated upper limit of autoregulation (ULA) value, and wherein the processing circuitry is configured to generate at least one of the updated LLA value or the updated ULA value by at least applying the offset value to at least one of a calculated LLA value or a calculated ULA value based on the subsequently received blood pressure values representative of the blood pressure of the patient sensed after the second time.

Example 4

The device of example 3, further comprising a display device, wherein the processing circuitry is configured to control the display device to: display the at least one of the updated LLA value or the updated ULA value; and display at least one of a prior LLA value or a prior ULA value generated based on blood pressure values representative of blood pressure sensed prior to the second time.

Example 5

The device of any of examples 3 and 4, wherein the processing circuitry is configured to generate the updated LLA value and the updated ULA value based on measured blood pressure values representative of the blood pressure sensed after the second time and downweighted blood pressure values, the downweighted blood pressure values representative of the blood pressure sensed prior to the second time.

Example 6

The device of any of examples 1 through 5, wherein the processing circuitry is configured to, in response to determining that the second blood pressure is greater than or equal to the threshold value, control a user interface to present a notification that indicates autoregulation information generated based on blood pressure values received prior to the second time is inaccurate.

Example 7

The device of any of examples 1 through 6, wherein the processing circuitry is configured to, in response to determining that the second blood pressure exceeds the threshold value, control a user interface to: display first autoregulation information generated based on blood pressure values representing the blood pressure sensed prior to the second time in greyscale; and display second autoregulation information generated based on blood pressure values representing the blood pressure sensed after, and including, the second time in one or more colors different than the greyscale.

Example 8

The device of any of examples 1 through 7, wherein the processing circuitry is configured to, in response to determining that the second blood pressure exceeds the threshold value, control a user interface to present a warning that indicates a blood pressure anomaly due to movement of a probe of the blood pressure sensor relative to the patient.

Example 9

The device of any of examples 1 through 8, wherein the difference comprises a difference rate of change of the blood pressure over a period of time between the first time and the second time, and the threshold comprises a threshold rate of change.

Example 10

The device of any of examples 1 through 9, wherein the processing circuitry is configured to generate the offset value by at least: receiving a movement signal from the blood pressure sensor representative of movement of a probe of the blood pressure sensor with respect to a blood vessel within which the blood pressure sensor is disposed; comparing a characteristic of the movement signal to a movement threshold; determining that the characteristic of the movement signal is greater than or equal to the movement threshold; and in response to determining that the characteristic of the movement signal is greater than or equal to the movement threshold and the difference value is greater than or equal to the threshold value, generating the offset value.

Example 11

The device of any of examples 1 through 10, further comprising a display device, wherein the processing circuit is configured to control the display device to display the updated parameter value.

Example 12

A method comprising: storing, by a memory, a first blood pressure value representative of a blood pressure of a patient sensed by a blood pressure sensor at a first time; receiving, by processing circuitry, a second blood pressure value representative of the blood pressure of the patient sensed by the blood pressure sensor at a second time; determining, by the processing circuitry, a difference value between the first blood pressure value and the second blood pressure value; determining, by the processing circuitry, that the difference value is greater than or equal to a threshold value; responsive to determining that the difference value is greater than or equal to the threshold value, generating, by the processing circuitry, an offset value that compensates for the difference value; generating, by the processing circuitry and based on the offset value and subsequently received blood pressure values representative of the blood pressure of the patient sensed after the second time, at least one updated parameter value; and outputting, by the processing circuitry, the at least one updated parameter value.

Example 13

The method of example 12, wherein the at least one updated parameter value comprises updated blood pressure values, and wherein generating the at least one updated parameter value comprises applying the offset value to the second blood pressure value and the subsequently received blood pressure values representative of the blood pressure of the patient sensed after the second time.

Example 14

The method of any of examples 12 and 13, wherein the at least one updated parameter value comprises at least one of an updated lower limit of autoregulation (LLA) value or an updated upper limit of autoregulation (ULA) value, and wherein generating the at least one updated parameter value comprises generating at least one of the updated LLA value or the updated ULA value by at least applying the offset value to at least one of a calculated LLA value or a calculated ULA value based on the subsequently received blood pressure values representative of the blood pressure of the patient sensed after the second time.

Example 15

The method of example 14, wherein generating the at least one updated parameter value comprises generating the updated LLA value and the updated ULA value based on measured blood pressure values representative of the blood pressure sensed after the second time and downweighted blood pressure values, the downweighted blood pressure values representative of the blood pressure sensed prior to the second time.

Example 16

The method of any of examples 12 through 15, further comprising, in response to determining that the second blood pressure is greater than or equal to the threshold value, controlling a user interface to present a warning that indicates autoregulation information based on blood pressure values received prior to the second time is inaccurate.

Example 17

The method of any of examples 12 through 16, further comprising, in response to determining that the second blood pressure is greater than or equal to the threshold value, controlling a user interface to: display first autoregulation information generated based on blood pressure values representing the blood pressure sensed prior to the second time in greyscale; and display second autoregulation information generated based on blood pressure values representing the blood pressure sensed after, and including, the second time in one or more colors different than the greyscale.

Example 18

The method of any of examples 12 through 17, wherein generating the offset value comprises: receiving a movement signal from the blood pressure sensor representative of movement of a probe of the blood pressure sensor with respect to a blood vessel within which the blood pressure sensor is disposed; comparing a characteristic of the movement signal to a movement threshold; determining that the characteristic of the movement signal is greater than or equal to the movement threshold; and in response to determining that the characteristic of the movement signal is greater than or equal to the movement threshold and the difference value is greater than or equal to the threshold value, generating the offset value.

Example 19

The method of any of examples 12 through 18, further comprising controlling a display device to display the updated parameter value.

Example 20

A system comprising: a memory configured to store a first blood pressure value representative of a blood pressure of a patient sensed by a blood pressure sensor at a first time; a display device configured to display autoregulation information; and processing circuitry configured to: receive a second blood pressure value representative of the blood pressure of the patient sensed by the blood pressure sensor at a second time; determine a difference value between the first blood pressure value and the second blood pressure value; determine that the difference value is greater than or equal to a threshold value; responsive to determining that the difference value is greater than or equal to the threshold value, control the display device to present an indication that indicates the autoregulation information based on blood pressure values representing the blood pressure sensed prior to the second time is inaccurate.

Example 21

The system of example 20, wherein the processing circuitry is configured to present the indication that indicates the autoregulation information based on the blood pressure values received prior to the second time is inaccurate by at least: displaying the autoregulation information generated based on the blood pressure values representing the blood pressure sensed prior to the second time in greyscale; and displaying subsequent autoregulation information generated based on blood pressure values representing the blood pressure sensed after, and including, the second time in one or more colors different than the greyscale.

Example 22

The system of any of examples 20 and 21, wherein the processing circuitry is configured to: generate an offset value that compensates for the difference value between the first blood pressure value and the second blood pressure; generate updated blood pressure values by at least applying the offset value to the second blood pressure value and subsequently received blood pressure values representative of the blood pressure of the patient sensed after the second time; and control the display device to display the updated blood pressure values.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to devices 100 and 200, processing circuitry 110, 210, 214, and 216, memories 120 and 220, displays 132 and 232, sensing circuitries 140-142, circuitries 240 and 245, sensing devices 150, 151, 152, and 250, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in patient monitors, such as multiparameter patient monitors (MPMs) or other devices, remote servers, or other devices. The term "processor" or "processing circuitry" may generally refer to any of the foregoing logic circuitry, alone or in combination with other logic circuitry, or any other equivalent circuitry.

As used herein, the term "circuitry" refers to an ASIC, an electronic circuit, a processor (shared, dedicated, or group) and memory that execute one or more software or firmware programs, a combinational logic circuit, or other suitable components that provide the described functionality. The term "processing circuitry" refers one or more processors distributed across one or more devices. For example, "processing circuitry" can include a single processor or multiple processors on a device. "Processing circuitry" can also include processors on multiple devices, wherein the operations described herein may be distributed across the processors and devices.

Such hardware, software, firmware may be implemented within the same device or within separate devices to support the various operations and functions described in this disclosure. For example, any of the techniques or processes described herein may be performed within one device or at least partially distributed amongst two or more devices, such as between devices 100 and 200, processing circuitry 110, 210, 214, and 216, memories 120 and 220, sensing circuitries 140-142, and/or circuitries 240 and 245. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache). Elements of devices and circuitry described herein, including, but not limited to, devices 100 and 200, processing circuitry 110, 210, 214, and 216, memories 120 and 220, displays 132 and 232, sensing circuitries 140-142, circuitries 240 and 245, sensing devices 150-152 and 250 may be programmed with various forms of software. The one or more processors may be implemented at least in part as, or include, one or more executable applications, application modules, libraries, classes, methods, objects, routines, subroutines, firmware, and/or embedded code, for example.

Various examples of the disclosure have been described. Any combination of the described systems, operations, or functions is contemplated. These and other examples are within the scope of the following claims.

What is claimed is:

1. A device comprising:
a memory configured to store a first blood pressure value representative of a blood pressure of a patient sensed by a blood pressure sensor at a first time;
processing circuitry configured to:
receive a second blood pressure value representative of the blood pressure of the patient sensed by the blood pressure sensor at a second time;
determine a difference value between the first blood pressure value and the second blood pressure value;
determine that the difference value is greater than or equal to a threshold value;
responsive to determining that the difference value is greater than or equal to the threshold value, generate an offset value that compensates for the difference value; and
generate, based on the offset value and subsequently received blood pressure values representative of the blood pressure of the patient sensed after the second time, at least one of an updated lower limit of autoregulation (LLA) value or an updated upper limit of autoregulation (ULA) value, wherein the processing circuitry is configured to generate the at least one of the updated LLA value or the updated ULA value by at least applying the offset value to at least one of a calculated LLA value or a calculated ULA value based on the subsequently received blood pressure values representative of the blood pressure of the patient sensed after the second time; and
a display device, wherein the processing circuitry is configured to control the display device to:
display the at least one of the updated LLA value or the updated ULA value; and
display at least one of a prior LLA value or a prior ULA value generated based on blood pressure values representative of blood pressure sensed prior to the second time.

2. The device of claim 1, wherein the processing circuitry is configured to generate the at least one of the updated LLA value or the updated ULA value based on measured blood pressure values representative of the blood pressure sensed after the second time and downweighted blood pressure values, the downweighted blood pressure values representative of the blood pressure sensed prior to the second time.

3. The device of claim 1, wherein the processing circuitry is configured to, in response to determining that the difference value is greater than or equal to the threshold value, control a user interface to present a notification that indicates autoregulation information generated based on blood pressure values received prior to the second time is inaccurate.

4. The device of claim 1, wherein the processing circuitry is configured to, in response to determining that the difference value exceeds the threshold value, control the display device to:
display first autoregulation information generated based on blood pressure values representing the blood pressure sensed prior to the second time in greyscale; and
display second autoregulation information generated based on blood pressure values representing the blood pressure sensed after, and including, the second time in one or more colors different than the greyscale.

5. The device of claim 1, wherein the processing circuitry is configured to, in response to determining that the difference value is greater than or equal to the threshold value, control a user interface to present a warning that indicates a blood pressure anomaly due to movement of a probe of the blood pressure sensor relative to the patient.

6. The device of claim 5, wherein the difference value comprises a difference rate of change of the blood pressure over a period of time between the first time and the second time, and the threshold comprises a threshold rate of change.

7. The device of claim 5, wherein the processing circuitry is configured to generate the offset value by at least:
receiving a movement signal from the blood pressure sensor representative of movement of a probe of the blood pressure sensor with respect to a blood vessel within which the blood pressure sensor is disposed;

comparing a characteristic of the movement signal to a movement threshold;
determining that the characteristic of the movement signal is greater than or equal to the movement threshold; and
in response to determining that the characteristic of the movement signal is greater than or equal to the movement threshold and the difference value is greater than or equal to the threshold value, generating the offset value.

8. A method comprising:
storing, by a memory, a first blood pressure value representative of a blood pressure of a patient sensed by a blood pressure sensor at a first time;
receiving, by processing circuitry, a second blood pressure value representative of the blood pressure of the patient sensed by the blood pressure sensor at a second time;
determining, by the processing circuitry, a difference value between the first blood pressure value and the second blood pressure value;
determining, by the processing circuitry, that the difference value is greater than or equal to a threshold value;
responsive to determining that the difference value is greater than or equal to the threshold value, generating, by the processing circuitry, an offset value that compensates for the difference value;
generating, by the processing circuitry and based on the offset value and subsequently received blood pressure values representative of the blood pressure of the patient sensed after the second time, at least one of an updated lower limit of autoregulation (LLA) value or an updated upper limit of autoregulation (ULA) value, wherein generating the at least one of the updated LLA value or the updated ULA value comprises applying the offset value to at least one of a calculated LLA value or a calculated ULA value based on the subsequently received blood pressure values representative of the blood pressure of the patient sensed after the second time; and
controlling, by the processing circuitry, a display device to:
display the at least one of the updated LLA value or the updated ULA value; and
display at least one of a prior LLA value or a prior ULA value generated based on blood pressure values representative of blood pressure sensed prior to the second time.

9. The method of claim 8, wherein generating the at least one of the updated LLA value or the updated ULA value comprises generating the at least one of the updated LLA value or the updated ULA value based on measured blood pressure values representative of the blood pressure sensed after the second time and downweighted blood pressure values, the downweighted blood pressure values representative of the blood pressure sensed prior to the second time.

10. The method of claim 8, further comprising, in response to determining that the difference value is greater than or equal to the threshold value, controlling a user interface to present a warning that indicates autoregulation information based on blood pressure values received prior to the second time is inaccurate.

11. The method of claim 8, further comprising, in response to determining that the difference value is greater than or equal to the threshold value, controlling the display device to:
display first autoregulation information generated based on blood pressure values representing the blood pressure sensed prior to the second time in greyscale; and
display second autoregulation information generated based on blood pressure values representing the blood pressure sensed after, and including, the second time in one or more colors different than the greyscale.

12. The method of claim 8, wherein generating the offset value comprises:
receiving a movement signal from the blood pressure sensor representative of movement of a probe of the blood pressure sensor with respect to a blood vessel within which the blood pressure sensor is disposed;
comparing a characteristic of the movement signal to a movement threshold;
determining that the characteristic of the movement signal is greater than or equal to the movement threshold; and
in response to determining that the characteristic of the movement signal is greater than or equal to the movement threshold and the difference value is greater than or equal to the threshold value, generating the offset value.

13. A system comprising:
a memory configured to store a first blood pressure value representative of a blood pressure of a patient sensed by a blood pressure sensor at a first time;
a display device configured to display autoregulation information; and
processing circuitry configured to:
receive a second blood pressure value representative of the blood pressure of the patient sensed by the blood pressure sensor at a second time;
determine a difference value between the first blood pressure value and the second blood pressure value;
determine that the difference value is greater than or equal to a threshold value;
responsive to determining that the difference value is greater than or equal to the threshold value, control the display device to present an indication that indicates the autoregulation information based on blood pressure values representing the blood pressure sensed prior to the second time is inaccurate;
responsive to determining that the difference value is greater than or equal to the threshold value, generate an offset value that compensates for the difference value;
generate, based on the offset value and subsequently received blood pressure values representative of the blood pressure of the patient sensed after the second time, at least one of an updated lower limit of autoregulation (LLA) value or an updated upper limit of autoregulation (ULA) value, wherein generating the at least one of the updated LLA value or the updated ULA value comprises applying the offset value to at least one of a calculated LLA value or a calculated ULA value based on the subsequently received blood pressure values representative of the blood pressure of the patient sensed after the second time; and
control the display device to display the at least one of the updated LLA value or the updated ULA value.

14. The system of claim 13, wherein the processing circuitry is configured to present the indication that indicates the autoregulation information based on the blood pressure values received prior to the second time is inaccurate by at least controlling the display device to:

display the autoregulation information generated based on the blood pressure values representing the blood pressure sensed prior to the second time in greyscale; and
display subsequent autoregulation information generated based on blood pressure values representing the blood pressure sensed after, and including, the second time in one or more colors different than the greyscale.

* * * * *